United States Patent
Brown, Jr. et al.

(10) Patent No.: US 12,163,129 B2
(45) Date of Patent: Dec. 10, 2024

(54) ANTISENSE OLIGONUCLEOTIDES TO RESTORE DYSFERLIN PROTEIN EXPRESSION IN DYSFERLINOPATHY PATIENT CELLS

(71) Applicant: University of Massachusetts, Boston, MA (US)

(72) Inventors: Robert H. Brown, Jr., Worcester, MA (US); Janice A. Dominov, Worcester, MA (US)

(73) Assignee: University of Massachusetts, Boston, MA (US)

( * ) Notice: Subject to any disclaimer, the term of this patent is extended or adjusted under 35 U.S.C. 154(b) by 950 days.

(21) Appl. No.: 16/972,655

(22) PCT Filed: Jun. 7, 2019

(86) PCT No.: PCT/US2019/036045
§ 371 (c)(1),
(2) Date: Dec. 7, 2020

(87) PCT Pub. No.: WO2019/236995
PCT Pub. Date: Dec. 12, 2019

(65) Prior Publication Data
US 2021/0246443 A1    Aug. 12, 2021

Related U.S. Application Data

(60) Provisional application No. 62/682,681, filed on Jun. 8, 2018.

(51) Int. Cl.
| | |
|---|---|
| *C12N 15/113* | (2010.01) |
| *A61P 21/00* | (2006.01) |
| *C12N 15/86* | (2006.01) |
| *C12Q 1/6883* | (2018.01) |

(52) U.S. Cl.
CPC ............ *C12N 15/113* (2013.01); *A61P 21/00* (2018.01); *C12N 15/86* (2013.01); *C12Q 1/6883* (2013.01); *C12N 2310/11* (2013.01); *C12N 2310/315* (2013.01); *C12N 2310/321* (2013.01); *C12N 2310/322* (2013.01); *C12N 2310/3231* (2013.01); *C12N 2310/3233* (2013.01); *C12N 2310/346* (2013.01); *C12N 2320/33* (2013.01); *C12N 2750/14143* (2013.01); *C12Q 2600/156* (2013.01)

(58) Field of Classification Search
None
See application file for complete search history.

(56) References Cited

U.S. PATENT DOCUMENTS

| | | |
|---|---|---|
| 5,470,967 A | 11/1995 | Huie et al. |
| 5,478,745 A | 12/1995 | Samulski et al. |
| 5,871,982 A | 2/1999 | Wilson et al. |
| 6,251,677 B1 | 6/2001 | Wilson et al. |
| 6,485,966 B2 | 11/2002 | Gao et al. |
| 6,544,786 B1 | 4/2003 | Xiao et al. |
| 6,673,909 B1 | 1/2004 | Brown et al. |
| 6,953,690 B1 | 10/2005 | Gao et al. |
| 7,022,519 B2 | 4/2006 | Gao et al. |
| 7,235,393 B2 | 6/2007 | Gao et al. |
| 7,427,396 B2 | 9/2008 | Arbetman et al. |
| 7,456,015 B2 | 11/2008 | Bohn et al. |
| 7,906,111 B2 | 3/2011 | Wilson et al. |
| 8,222,221 B2 | 7/2012 | Corey et al. |
| 8,524,446 B2 | 9/2013 | Gao et al. |
| 8,734,809 B2 | 5/2014 | Gao et al. |
| 9,217,155 B2 | 12/2015 | Gao et al. |
| 9,249,424 B2 | 2/2016 | Wolf et al. |
| 10,689,653 B2 | 6/2020 | Brown et al. |
| 11,827,886 B2 | 11/2023 | Brown et al. |
| 2001/0016355 A1 | 8/2001 | Samulski et al. |
| 2002/0164783 A1 | 11/2002 | Feldhaus |
| 2002/0192823 A1 | 12/2002 | Bartlett |
| 2003/0103939 A1 | 6/2003 | Engelhardt et al. |
| 2003/0110526 A1 | 6/2003 | Brown et al. |
| 2003/0138772 A1 | 7/2003 | Gao et al. |
| 2004/0101514 A1 | 5/2004 | Liu et al. |
| 2004/0123343 A1 | 6/2004 | La Rosa et al. |
| 2004/0219528 A1 | 11/2004 | Morris et al. |
| 2005/0032219 A1 | 2/2005 | Aubourg et al. |
| 2005/0197313 A1 | 9/2005 | Roelvink et al. |

(Continued)

FOREIGN PATENT DOCUMENTS

| | | |
|---|---|---|
| EP | 2261242 A1 | 12/2010 |
| WO | WO 2003/042397 A2 | 5/2003 |

(Continued)

OTHER PUBLICATIONS

Ni S, Yao H, Wang L, Lu J, Jiang F, Lu A, Zhang G. Chemical Modifications of Nucleic Acid Aptamers for Therapeutic Purposes. International Journal of Molecular Sciences. 2017; 18(8):1683. https://doi.org/10.3390/ijms18081683 (Year: 2017).*

International Search Report and Written Opinion for Application No. PCT/US2015/033973, mailed Sep. 29, 2015.

International Preliminary Report on Patentability for Application No. PCT/US2015/033973, mailed Dec. 15, 2016.

International Search Report and Written Opinion for Application No. PCT/US2019/036045, mailed Nov. 5, 2019.

International Preliminary Report on Patentability for Application No. PCT/US2019/036045, mailed Dec. 17, 2020.

Aartsma-Rus et al., New insights in gene-derived therapy: the example of Duchenne muscular dystrophy. Ann N Y Acad Sci. Dec. 2010;1214:199-212. doi: 10.1111/j.1749-6632.2010.05836.x. Epub Dec. 1, 2010.

(Continued)

*Primary Examiner* — Allison M Fox
*Assistant Examiner* — Alyssa G Weston
(74) *Attorney, Agent, or Firm* — Wolf, Greenfield & Sacks, P.C.

(57) ABSTRACT

The relates, in some aspects, to antisense oligonucleotide compositions and methods for modifying pre-mRNA splicing in a DYSF gene using the same. In some embodiments, the DYSF gene comprises a novel mutation that results in a pseudoexon between exons 50 and 51.

16 Claims, 8 Drawing Sheets

Specification includes a Sequence Listing.

(56) References Cited

U.S. PATENT DOCUMENTS

| | | |
|---|---|---|
| 2005/0255086 A1 | 11/2005 | Davidson et al. |
| 2005/0255089 A1 | 11/2005 | Chiorini et al. |
| 2006/0063174 A1 | 3/2006 | Turner et al. |
| 2006/0093589 A1 | 5/2006 | Warrington et al. |
| 2006/0153826 A1 | 7/2006 | Arnould et al. |
| 2006/0189564 A1 | 8/2006 | Burright et al. |
| 2006/0228800 A1 | 10/2006 | Lin et al. |
| 2006/0292117 A1 | 12/2006 | Loiler et al. |
| 2007/0036760 A1 | 2/2007 | Wilson et al. |
| 2007/0243526 A1 | 10/2007 | Kay et al. |
| 2007/0292410 A1 | 12/2007 | Cashman et al. |
| 2009/0042828 A1 | 2/2009 | Xu et al. |
| 2009/0111766 A1 | 4/2009 | Atkinson et al. |
| 2009/0149409 A1 | 6/2009 | Bohn et al. |
| 2009/0215879 A1 | 8/2009 | DiPrimio et al. |
| 2010/0266551 A1 | 10/2010 | Richard et al. |
| 2010/0323001 A1 | 12/2010 | Pachuk |
| 2011/0171262 A1 | 7/2011 | Bakker et al. |
| 2011/0172293 A1 | 7/2011 | Fish et al. |
| 2011/0212520 A1 | 9/2011 | Davidson et al. |
| 2011/0258716 A1 | 10/2011 | Baltimore et al. |
| 2012/0077870 A1 | 3/2012 | Blanks et al. |
| 2012/0137379 A1 | 5/2012 | Gao et al. |
| 2012/0208865 A1 | 8/2012 | Levy et al. |
| 2012/0270930 A1 | 10/2012 | Van Der Maarel et al. |
| 2012/0309050 A1 | 12/2012 | Kumon et al. |
| 2013/0030042 A1 | 1/2013 | Couto |
| 2013/0101558 A1 | 4/2013 | Gao et al. |
| 2013/0109742 A1 | 5/2013 | Hewitt et al. |
| 2013/0195801 A1 | 8/2013 | Gao et al. |
| 2013/0281516 A1 | 10/2013 | Gao et al. |
| 2013/0323226 A1 | 12/2013 | Wilson et al. |
| 2014/0142161 A1 | 5/2014 | Flotte et al. |
| 2014/0142288 A1 | 5/2014 | Davidson et al. |
| 2014/0179770 A1 | 6/2014 | Zhang et al. |
| 2014/0201857 A1 | 7/2014 | Fahrenkrug et al. |
| 2014/0296486 A1 | 10/2014 | Gao et al. |
| 2014/0335054 A1 | 11/2014 | Gao et al. |
| 2015/0065560 A1 | 3/2015 | Bjorklund et al. |
| 2016/0017005 A1 | 1/2016 | Asokan et al. |
| 2016/0060624 A1 | 3/2016 | Davidson et al. |
| 2016/0076054 A1 | 3/2016 | Auricchio et al. |
| 2016/0135438 A1 | 5/2016 | Gao et al. |
| 2016/0153005 A1 | 6/2016 | Zhang et al. |
| 2016/0185832 A1 | 6/2016 | Drivas et al. |
| 2016/0186211 A1 | 6/2016 | Flotte et al. |
| 2016/0194374 A1 | 7/2016 | Wijnholds et al. |
| 2016/0208257 A1 | 7/2016 | Gao et al. |
| 2016/0272976 A1 | 9/2016 | Kaspar |
| 2017/0029785 A1 | 2/2017 | Zhao et al. |
| 2017/0101645 A1 | 4/2017 | Brown et al. |
| 2017/0114340 A1 | 4/2017 | Mueller et al. |
| 2017/0165377 A1 | 6/2017 | Gao et al. |
| 2020/0339999 A1 | 10/2020 | Brown et al. |

FOREIGN PATENT DOCUMENTS

| | | |
|---|---|---|
| WO | WO 2005/033321 | 4/2005 |
| WO | WO 2006/031267 A2 | 3/2006 |
| WO | WO 2006/066066 A2 | 6/2006 |
| WO | WO 2006/119432 A2 | 11/2006 |
| WO | WO 2008/125846 A2 | 10/2008 |
| WO | WO 2008/150897 A2 | 12/2008 |
| WO | WO 2009/043936 A1 | 4/2009 |
| WO | WO 2009/146178 A1 | 12/2009 |
| WO | WO 2010/071454 A1 | 6/2010 |
| WO | WO 2010/099383 A2 | 9/2010 |
| WO | WO 2010/129021 A1 | 11/2010 |
| WO | WO 2010/138263 A2 | 12/2010 |
| WO | WO 2011/094198 A1 | 8/2011 |
| WO | WO 2013/055865 A1 | 4/2013 |
| WO | WO 2013/123503 A1 | 8/2013 |
| WO | WO 2013/190059 A1 | 12/2013 |
| WO | WO 2014/160092 A1 | 10/2014 |
| WO | WO 2014/186746 A1 | 11/2014 |
| WO | WO 2015/121501 A1 | 8/2015 |
| WO | WO 2015/164786 A1 | 10/2015 |
| WO | WO 2015/168666 A2 | 11/2015 |
| WO | WO 2015/187825 A2 | 12/2015 |
| WO | WO 2016/054615 A2 | 4/2016 |
| WO | WO 2016/065001 A1 | 4/2016 |
| WO | WO 2017/023724 A1 | 2/2017 |
| WO | WO 2017/106292 A1 | 6/2017 |

OTHER PUBLICATIONS

Alisky et al., Gene therapy for amyotrophic lateral sclerosis and other motor neuron diseases. Hum Gene Ther. Nov. 20, 2000;11(17):2315-29.

Arbuthnot et al., Hepatic delivery of RNA interference activators for therapeutic application. Curr Gene Ther. Apr. 2009;9(2):91-103.

Asokan et al., The AAV vector toolkit: poised at the clinical crossroads. Mol Ther. Apr. 2012;20(4):699-708. doi: 10.1038/mt.2011.287. Epub Jan. 24, 2012.

Azzouz et al., VEGF delivery with retrogradely transported lentivector prolongs survival in a mouse ALS model. Nature. May 27, 2004;429(6990):413-7.

Baek et al., AAV-mediated gene delivery in adult GM1-gangliosidosis mice corrects lysosomal storage in CNS and improves survival. PLoS One. Oct. 18, 2010;5(10):e13468. doi: 10.1371/journal.pone.0013468.

Berns et al., Biology of adeno-associated virus. Curr Top Microbiol Immunol. 1996;218:1-23.

Beutler et al., AAV for pain: steps towards clinical translation. Gene Ther. Apr. 2009;16(4):461-9. Epub Mar. 5, 2009.

Blandin et al., UMD-DYSF, a novel locus specific database for the compilation and interactive analysis of mutations in the dysferlin gene. Hum Mutat. Mar. 2012;33(3):E2317-31. doi: 10.1002/humu.22015. Epub Dec. 29, 2011.

Boillée et al., Onset and progression in inherited ALS determined by motor neurons and microglia. Science. Jun. 2, 2006;312(5778):1389-92.

Bourdenx et al., Systemic gene delivery to the central nervous system using Adeno-associated virus. Front Mol Neurosci. Jun. 2, 2014;7:50. doi: 10.3389/fnmol.2014.00050. eCollection 2014.

Buning et al., Receptor targeting of adeno-associated virus vectors. Gene Ther. Jul. 2003;10(14):1142-51.

Calcedo et al., Worldwide epidemiology of neutralizing antibodies to adeno-associated viruses. J Infect Dis. Feb. 1, 2009;199(3):381-90.

Carter et al., Adeno-associated virus gene expression and regulation. CRC Handbook of parvoviruses. 1990:227-54.

Carter, in "Handbook of Parvoviruses", ed., P. Tijsser, CRC Press, pp. 155-168 (1990).

Cearley et al., Expanded repertoire of AAV vector serotypes mediate unique patterns of transduction in mouse brain. Mol Ther. Oct. 2008;16(10):1710-8. doi: 10.1038/mt.2008.166. Epub Aug. 19, 2008.

Chadderton et al., Improved retinal function in a mouse model of dominant retinitis pigmentosa following AAV-delivered gene therapy. Mol Ther. Apr. 2009;17(4):593-9. Epub Jan. 27, 2009.

Chen et al., Molecular signatures of disease brain endothelia provide new sites for CNS-directed enzyme therapy. Nat Med. Oct. 2009;15(10):1215-8. doi: 10.1038/nm.2025. Epub Sep. 13, 2009.

Cheng et al., Development of optimized AAV3 serotype vectors: mechanism of high-efficiency transduction of human liver cancer cells. Gene Ther. Apr. 2012;19(4):375-84. doi: 10.1038/gt.2011.105. Epub Jul. 21, 2011.

Chiorini et al., Cloning and characterization of adeno-associated virus type 5. J Virol. Feb. 1999;73(2):1309-19.

Choudhury et al., Identification of Novel vectors capable of CNS transduction in adult mice after single round selection using DNA shuffled AAV capsid library. Mol Ther. May 1, 2013;21(1):S1.

Conlon et al., Ribozyme Approaches towards Down-Regulation of Pi*Z Mutant Human a-1 Anti-Trypsin. Mol. Therapy. 2004;9:S333. Abstract 875.

Cruz et al., The promise of gene therapy for the treatment of alpha-1 antitrypsin deficiency. Pharmacogenomics. Sep. 2007;8(9):1191-8.

(56) References Cited

OTHER PUBLICATIONS

Davidoff et al., Sex significantly influences transduction of murine liver by recombinant adeno-associated viral vectors through an androgen-dependent pathway. Blood. Jul. 15, 2003;102(2):480-8. Epub Mar. 13, 2003.

Daya et al., Gene therapy using adeno-associated virus vectors. Clin Microbiol Rev. Oct. 2008;21(4):583-93. doi: 10.1128/CMR.00008-08.

Di Giorgio et al., Non-cell autonomous effect of glia on motor neurons in an embryonic stem cell-based ALS model. Nat Neurosci. May 2007;10(5):608-14. Epub Apr. 15, 2007.

Dominov et al., A novel dysferlin mutant pseudoexon bypassed with antisense oligonucleotides. Ann Clin Transl Neurol. Sep. 2014;1(9):703-20. doi: 10.1002/acn3.96. Epub Sep. 27, 2014.

Duque et al., Intravenous administration of self-complementary AAV9 enables transgene delivery to adult motor neurons. Mol Ther. Jul. 2009;17(7):1187-96. doi: 10.1038/mt.2009.71. Epub Apr. 14, 2009.

Eberling et al., Results from a phase I safety trial of hAADC gene therapy for Parkinson disease. Neurology. May 20, 2008;70(21):1980-3. doi: 10.1212/01.wnl.0000312381.29287.ff. Epub Apr. 9, 2008.

Fechner et al., Cardiac-targeted RNA interference mediated by an AAV9 vector improves cardiac function in coxsackievirus B3 cardiomyopathy. J Mol Med (Berl). Sep. 2008;86(9):987-97. doi: 10.1007/s00109-008-0363-x. Epub Jun. 12, 2008.

Feigin et al., Modulation of metabolic brain networks after subthalamic gene therapy for Parkinson's disease. Proc Natl Acad Sci U S A. Dec. 4, 2007;104(49):19559-64. Epub Nov. 27, 2007.

Fisher et al., Transduction with recombinant adeno-associated virus for gene therapy is limited by leading-strand synthesis. J Virol. Jan. 1996;70(1):520-32.

Flotte et al., Phase I trial of intramuscular injection of a recombinant adeno-associated virus alpha 1-antitrypsin (rAAV2-CB-hAAT) gene vector to AAT-deficient adults. Hum Gene Ther. Jan. 2004;15(1):93-128.

Foust et al., Intravascular AAV9 preferentially targets neonatal-neurons and adult-astrocytes. Nature Biotechnology, 27; 59-65 2009.

Foust et al., Over the barrier and through the blood: to CNS delivery we go. Cell Cycle. Dec. 15, 2009;8(24):4017-8.

Fraldi et al., Functional correction of CNS lesions in an MPS-IIIA mouse model by intracerebral AAV-mediated delivery of sulfamidase and SUMF1 genes. Hum Mol Genet. Nov. 15, 2007;16(22):2693-702. Epub Aug. 27, 2007.

Gadalla et al., Improved survival and reduced phenotypic severity following AAV9/MECP2 gene transfer to neonatal and juvenile male Mecp2 knockout mice. Mol Ther. Jan. 2013;21(1):18-30. doi:10.1038/mt.2012.200. Epub Sep. 25, 2012.

Gao et al., Inadvertent gene transfer of co-packaged rep and cap sequences during the production of AAV vector and its potential impact on vector performance. Molecular Therapy. May 2008;16(Suppl. 1):S105-S106. Abstract 279.

Gao et al., RAAV-mediated targeting in adult mice and its potential in generating animal models of tissue-specific somatic transgenics or knock down. Molecular Therapy. May 2008;16(1):S118-S119. Abstract 316.

Grimm, Small silencing RNAs: state-of-the-art. Adv Drug Deliv Rev. Jul. 25, 2009;61(9):672-703. doi: 10.1016/j.addr.2009.05.002. Epub May 7, 2009.

Iida et al., Systemic Delivery of Tyrosine-Mutant AAV Vectors Results in Robust Transduction of Neurons in Adult Mice. BioMed Res Int. 2013;2013.

Jakobsson et al., Lentiviral vectors for use in the central nervous system. Mol Ther. Mar. 2006;13(3):484-93. Epub Jan. 3, 2006.

Janson et al., Clinical protocol. Gene therapy of Canavan disease: AAV-2 vector for neurosurgical delivery of aspartoacylase gene (ASPA) to the human brain. Hum Gene Ther. Jul. 20, 2002;13(11):1391-412.

Kaspar et al., Retrograde viral delivery of IGF-1 prolongs survival in a mouse ALS model. Science. Aug. 8, 2003;301(5634):839-42.

Koornneef et al., Apolipoprotein B knockdown by AAV-delivered shRNA lowers plasma cholesterol in mice. Mol Ther. Apr. 2011;19(4):731-40. doi:10.1038/mt.2011.6. Epub Feb. 8, 2011.

Kotin et al., Organization of adeno-associated virus DNA in latently infected Detroit 6 cells. Virology. Jun. 1989;170(2):460-7.

Kotin et al., Site-specific integration by adeno-associated virus. Proc Natl Acad Sci U S A. Mar. 1990;87(6):2211-5.

Lawlor et al., Efficient gene delivery and selective transduction of glial cells in the mammalian brain by AAV serotypes isolated from nonhuman primates. Mol Ther. Oct. 2009;17(10):1692-702. doi:; 10.1038/mt.2009.170.

Li et al., Efficient and Targeted Transduction of Nonhuman Primate Liver With Systemically Delivered Optimized AAV3B Vectors. Mol Ther. Dec. 2015;23(12):1867-76. doi: 10.1038/mt.2015.174. Epub Sep. 25, 2015.

Li et al., Protein trans-splicing as a means for viral vector-mediated in vivo gene therapy. Hum Gene Ther. Sep. 2008;19(9):958-64. doi: 10.1089/hum.2008.009.

Lowenstein, Crossing the rubicon. Nat Biotechnol. Jan. 2009;27(1):42-4.

Lux et al., Green fluorescent protein-tagged adeno-associated virus particles allow the study of cytosolic and nuclear trafficking. J Virol. Sep. 2005;79(18):11776-87.

Maguire et al., Gene therapy for the nervous system: challenges and new strategies. Neurotherapeutics. Oct. 2014;11(4):817-39. doi: 10.1007/s13311-014-0299-5.

Mandel et al., Recombinant adeno-associated viral vectors as therapeutic agents to treat neurological disorders. Mol Ther. Mar. 2006;13(3):463-83. Epub Jan. 18, 2006.

Matalon et al., Adeno-associated virus-mediated aspartoacylase gene transfer to the brain of knockout mouse for canavan disease. Mol Ther. May 2003;7(5 Pt 1):580-7.

McBride et al., Artificial miRNAs mitigate shRNA-mediated toxicity in the brain: implications for the therapeutic development of RNAi. Proc Natl Acad Sci U S A. Apr. 15, 2008;105(15):5868-73. Epub Apr. 8, 2008.

McCarty et al., Adeno-associated virus terminal repeat (TR) mutant generates self-complementary vectors to overcome the rate-limiting step to transduction in vivo. Gene Ther. Dec. 2003;10(26):2112-8.

McCarty et al., Integration of adeno-associated virus (AAV) and recombinant AAV vectors. Annu Rev Genet. 2004;38:819-45.

McCarty et al., Self-complementary recombinant adeno-associated virus (scAAV) vectors promote efficient transduction independently of DNA synthesis. Gene Ther. Aug. 2001;8(16):1248-54.

McCarty, Self-complementary AAV vectors; advances and applications. Mol Ther. Oct. 2008;16(10):1648-56. Epub Aug. 5, 2008.

McCurdy et al., Sustained normalization of neurological disease after intracranial gene therapy in a feline model. Sci Transl Med. Apr. 9, 2014;6(231):231ra48. doi: 10.1126/scitranslmed.3007733.

Mietzsch et al., OneBac 2.0: Sf9 Cell Lines for Production of AAV5 Vectors with Enhanced Infectivity and Minimal Encapsidation of Foreign DNA. Hum Gene Ther. Oct. 2015;26(10):688-97. doi:10.1089/hum.2015.050. Epub Aug. 6, 2015.

Mueller et al., Development of Simultaneous Gene Augmentation and Reduction of Mutant Gene Expression with a Single Recombinant AAV for Alpha-1 Antitrypsin Disease. Molecular Therapy May 2009;17(1):S391-S392. Abstract 1030.

O'Reilly et al., RNA interference-mediated suppression and replacement of human rhodopsin in vivo. Am J Hum Genet. Jul. 2007;81(1):127-35. Epub May 23, 2007.

Passini et al., CNS-targeted gene therapy improves survival and motor function in a mouse model of spinal muscular atrophy. J Clin Invest. Apr. 2010;120(4):1253-64. doi: 10.1172/JCI41615. Epub Mar. 15, 2010.

Ralph et al., Silencing mutant SOD1 using RNAi protects against neurodegeneration and extends survival in an ALS model. Nat Med. Apr. 2005;11(4):429-33. Epub Mar. 13, 2005.

Raoul et al., Lentiviral-mediated silencing of SOD1 through RNA interference retards disease onset and progression in a mouse model of ALS. Nat Med. Apr. 2005;11(4):423-8. Epub Mar. 13, 2005.

(56) References Cited

OTHER PUBLICATIONS

Schattgen et al., Cutting Edge: DNA in the Lung Microenvironment during Influenza Virus Infection Tempers Inflammation by Engaging the DNA Sensor AIM2. J Immunol. Jan. 1, 2016;196(1):29-33. doi:10.4049/jimmunol.1501048.
Schnepp et al., Characterization of adeno-associated virus genomes isolated from human tissues. J Virol. Dec. 2005;79(23):14793-803.
Snyder et al., Comparison of adeno-associated viral vector serotypes for spinal cord and motor neuron gene delivery. Hum Gene Ther. Sep. 2011;22(9):1129-35. doi: 10.1089/hum.2011.008. Epub Jul. 25, 2011.
Stoica et al., Targeting Human SOD1 Using AAV mediated RNAi in a mouse model of amyotrophic lateral sclerosis. Mol ther. Jun. 2013;21(1):S149.
Storkebaum et al., Treatment of motoneuron degeneration by intracerebroventricular delivery of VEGF in a rat model of ALS. Nat Neurosci. Jan. 2005;8(1):85-92. Epub Nov. 28, 2004.
Tenenbaum et al., Recombinant AAV-mediated gene delivery to the central nervous system. J Gene Med. Feb. 2004;6 Suppl 1:S212-22.
Tomar et al., Use of adeno-associated viral vector for delivery of small interfering RNA. Oncogene. Aug. 28, 2003;22(36):5712-5.
Towne et al., Systemic AAV6 delivery mediating RNA interference against SOD1: neuromuscular transduction does not alter disease progression in fALS mice. Mol Ther. Jun. 2008;16(6):1018-25. doi: 10.1038/mt.2008.73. Epub Apr. 15, 2008.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
UNIPROT Submission; Accession No. A8IGP7; Nov. 13, 2013.
UNIPROT Submission; Accession No. H3GK32; Feb. 6, 2013.
UNIPROT Submission; Accession No. T2BRA8; Nov. 13, 2013.
Vandenberghe et al., Tailoring the AAV vector capsid for gene therapy. Gene Ther. Mar. 2009;16(3):311-9. Epub Dec. 4, 2008.
Vandendriessche et al., Efficacy and safety of adeno-associated viral vectors based on serotype 8 and 9 vs. lentiviral vectors for hemophilia B gene therapy. J Thromb Haemost. Jan. 2007;5(1):16-24. Epub Sep. 26, 2006.
Wang et al., Neuroprotective effects of glial cell line-derived neurotrophic factor mediated by an adeno-associated virus vector in a transgenic animal model of amyotrophic lateral sclerosis. J Neurosci. Aug. 15, 2002;22(16):6920-8.
Wang et al., Rescue and replication of adeno-associated virus type 2 as well as vector DNA sequences from recombinant plasmids containing deletions in the viral inverted terminal repeats: selective encapsidation of viral genomes in progeny virions. J Virol. Mar. 1996;70(3):1668-77.
Wang et al., Somatically Repairing Compound Heterozygous Recessive Mutations by Chromosomal Cut-and-Paste for in Vivo Gene Therapy. May 2016. 24(1):S289. Abstract 733.
Wang et al., The design of vectors for RNAi delivery system. Curr Pharm Des. 2008;14(13):1327-40.
Wang et al., The potential of adeno-associated viral vectors for gene delivery to muscle tissue. Expert Opin Drug Deliv. Mar. 2014;11(3):345-64. doi: 10.1517/17425247.2014.871258. Epub Jan. 3, 2014.
Wang et al., Therapeutic gene silencing delivered by a chemically modified small interfering RNA against mutant SOD1 slows amyotrophic lateral sclerosis progression. J Biol Chem. Jun. 6, 2008;283(23):15845-52. doi: 10.1074/jbc.M800834200. Epub Mar. 26, 2008.
Wang et al., Widespread spinal cord transduction by intrathecal injection of rAAV delivers efficacious RNAi therapy for amyotrophic lateral sclerosis. Hum Mol Genet. Feb. 1, 2014;23(3):668-81. doi: 10.1093/hmg/ddt454. Epub Sep. 18, 2013.
Watson et al., Intrathecal administration of AAV vectors for the treatment of lysosomal storage in the brains of MPS I mice. Gene Ther. Jun. 2006;13(11):917-25.
Wein et al., Efficient bypass of mutations in dysferlin deficient patient cells by antisense-induced exon skipping. Hum Mutat. Feb. 2010;31(2):136-42. doi: 10.1002/humu.21160.
Weismann et al., Systemic AAV9 gene transfer in adult GM1 gangliosidosis mice reduces lysosomal storage in CNS and extends lifespan. Hum Mol Genet. Aug. 1, 2015;24(15):4353-64. doi: 10.1093/hmg/ddv168. Epub May 10, 2015.
Weismann, Approaches and Considerations Towards a Safe and Effective Adena-Associated Virus Mediated Therapeutic Intervention for GM 1-Gangliosidosis: A Dissertation. University Massachusetts Medical School. Aug. 5, 2014.
Xia et al., Allele-specific RNAi selectively silences mutant SOD1 and achieves significant therapeutic benefit in vivo. Neurobiol Dis. Sep. 2006;23(3):578-86. Epub Jul. 20, 2006.
Xie et al., 676. DNA Sequences Encoding shRNAs Can Replace Mutant ITR in scAAV Genome for Efficient Replication and Packaging and Transcribe shRNAs by pol III Promoter Activity of wt ITR for Efficient Gene Silencing Mol Therapy. May 2015;23(1):S269.
Xie et al., Characterization of positioning effect of pol III-shRNA transcription unit in scAAV vector genome on the packaging efficiency and functionality of shRNA silencing. Molecular Therapy. May 2010;18(1): S262. Abstract 671.
Xie et al., rAAV-mediated delivery of micro RNA scavengers leads to efficient and stable knockdown of cognate micro RNAs, upregulation of their natural target genes and phenotypic changes in mice. Molecular Therapy. May 2010;18(1): S140. Abstract362.
Xie et al., Short DNA Hairpins Compromise Recombinant Adeno-Associated Virus Genome Homogeneity. Mol Ther. Jun. 7, 2017;25(6):1363-1374. doi: 10.1016/j.ymthe.2017.03.028. Epub Apr. 24, 2017.
Xu et al., Delivery of MDR1 small interfering RNA by self-complementary recombinant adeno-associated virus vector. Mol Ther. Apr. 2005;11(4):523-30.
Zincarelli et al., Analysis of AAV serotypes 1-9 mediated gene expression and tropism in mice after systemic injection. Mol Ther. Jun. 2008;16(6):1073-80. doi: 10.1038/mt.2008.76. Epub Apr. 15, 2008.
Zolotukhin et al., Production and purification of serotype 1, 2, and 5 recombinant adeno-associated viral vectors. Methods. Oct. 2002;28(2):158-67.
Extended European Search Report for Application No. 19814935.3, mailed Sep. 16, 2022.
Dominov et al., Correction of pseudoexon splicing caused by a novel intronic dysferlin mutation. Ann Clin Transl Neurol. Mar. 3, 2019;6(4):642-654. doi: 10.1002/acn3.738.

\* cited by examiner

SEQUENCE LISTING

```
<160> NUMBER OF SEQ ID NOS: 123

<210> SEQ ID NO 1
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 1
aggtgcaaaa tgccgtgt                                                 18

<210> SEQ ID NO 2
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 2
ttcacccctg caaacacc                                                 18

<210> SEQ ID NO 3
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 3
cacacccgac accgacat                                                 18

<210> SEQ ID NO 4
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 4
ctccgcctca tctccagtg                                                19
```

```
<210> SEQ ID NO 5
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 5
cgactctgcc tgacctgga                                              19

<210> SEQ ID NO 6
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 6
aatggtgccc acgtccat                                               18

<210> SEQ ID NO 7
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 7
tcgttctctc aggacagatg c                                           21

<210> SEQ ID NO 8
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 8
ctgagggttg gccgtctt                                               18

<210> SEQ ID NO 9
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 9
gacccctttg tggaggtca                                              19

<210> SEQ ID NO 10
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 10
gctccaccag cttggtctc                                              19

<210> SEQ ID NO 11
<211> LENGTH: 19
<212> TYPE: DNA
<213> ORGANISM: Artificial Sequence
<220> FEATURE:
<223> OTHER INFORMATION: Synthetic Polynucleotide
```

<400> SEQUENCE: 11 ggggaaggt gtggcttat                    19

<210> SEQ ID NO 12
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 12
cagcgagtcc acgtcctc                     18

<210> SEQ ID NO 13
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 13
ccagctgctt gggattgc                     18

<210> SEQ ID NO 14
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 14
tcccacaatt cttgccaca                    19

<210> SEQ ID NO 15
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 15
gcccaccaag tcctcttctc                   20

<210> SEQ ID NO 16
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 16
aagccgggtc tggttctc                     18

<210> SEQ ID NO 17
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 17
tcacctgagc ttcgtggaa                    19

<210> SEQ ID NO 18
<211> LENGTH: 19

<212> TYPE: DNA
<213> ORGANISM: Artificial Sequence
<220> FEATURE:
<223> OTHER INFORMATION: Synthetic Polynucleotide

<400> SEQUENCE: 18
ttctccagtg gctccatgc                                                    19

<210> SEQ ID NO 19
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 19
ccacctcgag taccgcaag                                                    19

<210> SEQ ID NO 20
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 20
cgtacagctc caccacaatg                                                   20

<210> SEQ ID NO 21
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 21 aacacccctta accccacctg                                                  20

<210> SEQ ID NO 22
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 22
cggaggttcc tgatgacaca                                                   20

<210> SEQ ID NO 23
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 23
ccccagcctc gtggtaga                                                     18

<210> SEQ ID NO 24
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 24

```
accttcaggg tgtcaaaatc c                                              21

<210> SEQ ID NO 25
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 25
tgcctccata ggggagagg                                                 19

<210> SEQ ID NO 26
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 26
tgcaggtcag ctcgaaca                                                  18

<210> SEQ ID NO 27
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 27
tggagcccgt atttggaa                                                  18

<210> SEQ ID NO 28
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 28 tgcaggggc tgtagagg                                                   18

<210> SEQ ID NO 29
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 29
cgtctggctc tgcatgtg                                                  18

<210> SEQ ID NO 30
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 30
ccactcgtgc tgggattttt                                                19

<210> SEQ ID NO 31
<211> LENGTH: 20
<212> TYPE: DNA
<213> ORGANISM: Artificial Sequence
```

<220> FEATURE:
<223> OTHER INFORMATION: Synthetic Polynucleotide

<400> SEQUENCE: 31
ctgccagctg agcaagtctg                                              20

<210> SEQ ID NO 32
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 32
gccgccacag gatgaact                                                18

<210> SEQ ID NO 33
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 33
ccgacacctc cttcctgtg                                               19

<210> SEQ ID NO 34
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 34
ttgtggttcc aactgtttta tactga                                       26

<210> SEQ ID NO 35
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 35
tgggaggtga aggcaactt                                               19

<210> SEQ ID NO 36
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 36 tggaaaggg gtggatgc                                                 18

<210> SEQ ID NO 37
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 37
tcatggcact accgtggtc                                               19

```
<210> SEQ ID NO 38
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 38
ggagggtgat ggctgtgg                                                    18

<210> SEQ ID NO 39
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 39
gcctatggtc accgtcca                                                    18

<210> SEQ ID NO 40
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 40
aatcgggcca gcagaatc                                                    18

<210> SEQ ID NO 41
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 41
gtcccacccg gcattaaa                                                    18

<210> SEQ ID NO 42
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 42
ttggggcaga tgcaacct                                                    18

<210> SEQ ID NO 43
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 43
gaaagcatgg gccgtttg                                                    18

<210> SEQ ID NO 44
<211> LENGTH: 18
<212> TYPE: DNA
<213> ORGANISM: Artificial Sequence
<220> FEATURE:
<223> OTHER INFORMATION: Synthetic Polynucleotide
```

```
<400> SEQUENCE: 44
aatggagcca ccccaaat                                                18

<210> SEQ ID NO 45
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 45
agagagggtt acccggcagt                                              20

<210> SEQ ID NO 46
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 46
gtttctgtct ccgccttcg                                               19

<210> SEQ ID NO 47
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 47
gggagaaggt ggctggaa                                                18

<210> SEQ ID NO 48
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 48
ctgacgtgca gggtgtgc                                                18

<210> SEQ ID NO 49
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 49
gcggctttga accaccac                                                18

<210> SEQ ID NO 50
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 50
agctcccgaa ccgaagac                                                18

<210> SEQ ID NO 51
```

```
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 51
ccaacccagg cagcagtc                                                   18

<210> SEQ ID NO 52
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 52
cagctcgcct ggaacaag                                                   18

<210> SEQ ID NO 53
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 53
cagtcccaca ccgctcag                                                   18

<210> SEQ ID NO 54
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 54
tatgcgttgg ccctctactg                                                 20

<210> SEQ ID NO 55
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 55
cagctgccag ggtttgag                                                   18

<210> SEQ ID NO 56
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 56
ggatgcaagg aagcaaggt                                                  19

<210> SEQ ID NO 57
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 57
```
cccttgggga catcctactc				20

<210> SEQ ID NO 58
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 58
acttgcgtcc ctcgcttac				19

<210> SEQ ID NO 59
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 59
cccggcactc aggacttg				18

<210> SEQ ID NO 60
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 60
tgctgggaag ttccgtctc				19

<210> SEQ ID NO 61
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 61
gtaaaacgac ggccagt				17

<210> SEQ ID NO 62
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 62
caggaaacag ctatgac				17

<210> SEQ ID NO 63
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 63
agucuuguuc ucuguuuucu ca				22

<210> SEQ ID NO 64
<211> LENGTH: 22
<212> TYPE: DNA

```
<213> ORGANISM: Artificial Sequence
<220> FEATURE:
<223> OTHER INFORMATION: Synthetic Polynucleotide

<400> SEQUENCE: 64
tgagaaaaca gagaacaaga ct                                              22

<210> SEQ ID NO 65
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 65
acugaggcuu cauggagcaa c                                               21

<210> SEQ ID NO 66
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 66
gttgctccat gaagcctcag t                                               21

<210> SEQ ID NO 67
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 67
ggucaucuug ggcuuccucc cac                                             23

<210> SEQ ID NO 68
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 68
gtgggaggaa gcccaagatg acc                                             23

<210> SEQ ID NO 69
<211> LENGTH: 24
<212> TYPE: RNA
<213> ORGANISM: Artificial Sequence
<220> FEATURE:
<223> OTHER INFORMATION: Synthetic Polynucleotide

<400> SEQUENCE: 69
cggaggccgg ggagcacccc ucag                                            24

<210> SEQ ID NO 70
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 70
ctgaggggtg ctccccggcc tccg                                            24
```

<210> SEQ ID NO 71
<211> LENGTH: 24
<212> TYPE: RNA
<213> ORGANISM: Artificial Sequence
<220> FEATURE:
<223> OTHER INFORMATION: Synthetic Polynucleotide

<400> SEQUENCE: 71
gagcaagggc cuggacccaa cucu                                            24

<210> SEQ ID NO 72
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 72
agagttgggt ccaggccctt gctc                                            24

<210> SEQ ID NO 73
<211> LENGTH: 24
<212> TYPE: RNA
<213> ORGANISM: Artificial Sequence
<220> FEATURE:
<223> OTHER INFORMATION: Synthetic Polynucleotide

<400> SEQUENCE: 73
ccaaguccug agugccgggu caga                                            24

<210> SEQ ID NO 74
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 74
tctgacccgg cactcaggac ttgg                                            24

<210> SEQ ID NO 75
<211> LENGTH: 24
<212> TYPE: RNA
<213> ORGANISM: Artificial Sequence
<220> FEATURE:
<223> OTHER INFORMATION: Synthetic Polynucleotide

<400> SEQUENCE: 75
gaccacccug cagauggugg gugc                                            24

<210> SEQ ID NO 76
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 76
gcacccacca tctgcagggt ggtc                                            24

<210> SEQ ID NO 77
<211> LENGTH: 24
<212> TYPE: RNA
<213> ORGANISM: Artificial Sequence
<220> FEATURE:

<223> OTHER INFORMATION: Synthetic Polynucleotide

<400> SEQUENCE: 77
uggcaaggac aggaaacagu guga                                          24

<210> SEQ ID NO 78
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 78
tcacactgtt tcctgtcctt gcca                                          24

<210> SEQ ID NO 79
<211> LENGTH: 24
<212> TYPE: RNA
<213> ORGANISM: Artificial Sequence
<220> FEATURE:
<223> OTHER INFORMATION: Synthetic Polynucleotide

<400> SEQUENCE: 79
acuauaacuc uccccugggu gagu                                          24

<210> SEQ ID NO 80
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 80
actcacccag gggagagtta tagt                                          24

<210> SEQ ID NO 81
<211> LENGTH: 24
<212> TYPE: RNA
<213> ORGANISM: Artificial Sequence
<220> FEATURE:
<223> OTHER INFORMATION: Synthetic Polynucleotide

<400> SEQUENCE: 81
gucacuaggg cuuuccagcg cagu                                          24

<210> SEQ ID NO 82
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 82
actgcgctgg aaagccctag tga                                           23

<210> SEQ ID NO 83
<211> LENGTH: 24
<212> TYPE: RNA
<213> ORGANISM: Artificial Sequence
<220> FEATURE:
<223> OTHER INFORMATION: Synthetic Polynucleotide

<400> SEQUENCE: 83
ccacacucaa cccacagcac uguc                                          24

```
<210> SEQ ID NO 84
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 84
gacagtgctg tgggttgagt gtgg                                          24

<210> SEQ ID NO 85
<211> LENGTH: 24
<212> TYPE: RNA
<213> ORGANISM: Artificial Sequence
<220> FEATURE:
<223> OTHER INFORMATION: Synthetic Polynucleotide

<400> SEQUENCE: 85
accccucagu ccagccacac ucaa                                          24

<210> SEQ ID NO 86
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 86
ttgagtgtgg ctggactgag gggt                                          24

<210> SEQ ID NO 87
<211> LENGTH: 24
<212> TYPE: RNA
<213> ORGANISM: Artificial Sequence
<220> FEATURE:
<223> OTHER INFORMATION: Synthetic Polynucleotide

<400> SEQUENCE: 87
ugagcggugu gggacugcac augc                                          24

<210> SEQ ID NO 88
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 88
gcatgtgcag tcccacaccg ctca                                          24

<210> SEQ ID NO 89
<211> LENGTH: 24
<212> TYPE: RNA
<213> ORGANISM: Artificial Sequence
<220> FEATURE:
<223> OTHER INFORMATION: Synthetic Polynucleotide

<400> SEQUENCE: 89
gggcuuccuc ccacugaggc uuca                                          24

<210> SEQ ID NO 90
<211> LENGTH: 24
<212> TYPE: DNA
<213> ORGANISM: Artificial Sequence
<220> FEATURE:
<223> OTHER INFORMATION: Synthetic Polynucleotide
```

<400> SEQUENCE: 90
tgaagcctca gtgggaggaa gccc                                              24

<210> SEQ ID NO 91
<211> LENGTH: 24
<212> TYPE: RNA
<213> ORGANISM: Artificial Sequence
<220> FEATURE:
<223> OTHER INFORMATION: Synthetic Polynucleotide

<400> SEQUENCE: 91
aggucaucuu gggcuuccuc ccac                                              24

<210> SEQ ID NO 92
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 92
gtgggaggaa gcccaagatg acct                                              24

<210> SEQ ID NO 93
<211> LENGTH: 24
<212> TYPE: RNA
<213> ORGANISM: Artificial Sequence
<220> FEATURE:
<223> OTHER INFORMATION: Synthetic Polynucleotide

<400> SEQUENCE: 93
ucagaccagc ucgccuggaa caag                                              24

<210> SEQ ID NO 94
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 94
cttgttccag gcgagctggt ctga                                              24

<210> SEQ ID NO 95
<211> LENGTH: 24
<212> TYPE: RNA
<213> ORGANISM: Artificial Sequence
<220> FEATURE:
<223> OTHER INFORMATION: Synthetic Polynucleotide

<400> SEQUENCE: 95
uucucucccc accccaccuc ccuc                                              24

<210> SEQ ID NO 96
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 96
gagggaggtg gggtggggag agaa                                              24

<210> SEQ ID NO 97
<211> LENGTH: 24

```
<212> TYPE: RNA
<213> ORGANISM: Artificial Sequence
<220> FEATURE:
<223> OTHER INFORMATION: Synthetic Polynucleotide

<400> SEQUENCE: 97
gcugaaagga gaggaggggc ccuu                                        24

<210> SEQ ID NO 98
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 98
aagggcccct cctctccttt cagc                                        24

<210> SEQ ID NO 99
<211> LENGTH: 24
<212> TYPE: RNA
<213> ORGANISM: Artificial Sequence
<220> FEATURE:
<223> OTHER INFORMATION: Synthetic Polynucleotide

<400> SEQUENCE: 99
agugcuggga aguuccgucu ccug                                        24

<210> SEQ ID NO 100
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 100
caggagacgg aacttcccag cact                                        24

<210> SEQ ID NO 101
<211> LENGTH: 24
<212> TYPE: RNA
<213> ORGANISM: Artificial Sequence
<220> FEATURE:
<223> OTHER INFORMATION: Synthetic Polynucleotide

<400> SEQUENCE: 101
gggcaaagcc aaagccugaa gugc                                        24

<210> SEQ ID NO 102
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 102
gcacttcagg ctttggcttt gccc                                        24

<210> SEQ ID NO 103
<211> LENGTH: 180
<212> TYPE: DNA
<213> ORGANISM: Artificial Sequence
<220> FEATURE:
<223> OTHER INFORMATION: Synthetic Polynucleotide

<400> SEQUENCE: 103
```

```
gggagagtta tagtgagaaa acagagaaca agactgcgct ggaaagccct agtgacagtg    60
ctgtgggttg agtgtggctg gactgagggg tgctccccgg cctccgcatg tgcagtccca   120
caccgctcag ttgctccatg aagcctcagt gggaggaagc ccaagatgac cttgttccag   180
```

<210> SEQ ID NO 104
<211> LENGTH: 279
<212> TYPE: DNA
<213> ORGANISM: Artificial Sequence
<220> FEATURE:
<223> OTHER INFORMATION: Synthetic Polynucleotide

<400> SEQUENCE: 104

```
caccatctgc agggtggtca cactgtttcc tgtccttgcc actcacccag gggagagtta    60
tagtgagaaa acagagaaca agactgcgct ggaaagccct agtgacagtg ctgtgggttg   120
agtgtggctg gactgagggg tgctccccgg cctccgcatg tgcagtccca caccgctcag   180
ttgctccatg aagcctcagt gggaggaagc ccaagatgac cttgttccag gcagctggtc   240
tgagggaggt ggggtgggga gagaagggcc cctcctctc                           279
```

<210> SEQ ID NO 105
<211> LENGTH: 278
<212> TYPE: DNA
<213> ORGANISM: Artificial Sequence
<220> FEATURE:
<223> OTHER INFORMATION: Synthetic Polynucleotide

<400> SEQUENCE: 105

```
caccatctgc agggtggtca cactgtttcc tgtccttgcc actcacccag gggagagtta    60
tagtgagaaa acagagaaca agactgcgct ggaaagccct agtgacagtg ctgtgggttg   120
agtgtggctg gactgagggg tgctccccgg cctccgcatg tgcagtccca caccgctcag   180
ttgctccatg aagcctcagt gggaggaagc ccaagatgac cttgttccag gagctggtct   240
gagggaggtg gggtggggag agaagggccc ctcctctc                            278
```

<210> SEQ ID NO 106
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 106

```
ttgttccagg cgagctggtc t                                              21
```

<210> SEQ ID NO 107
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 107

```
ttgttccagg tgagctggtc t                                              21
```

<210> SEQ ID NO 108
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 108

```
ctgtctcagc attgtgtgat g                                              21

<210> SEQ ID NO 109
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 109
ctgtctcagc gttgtgtgat g                                              21

<210> SEQ ID NO 110
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 110
tatgctggtt attgtgtgat g                                              21

<210> SEQ ID NO 111
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 111
tatgctggtt gttgtgtgat g                                              21

<210> SEQ ID NO 112
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 112 gcagggtgg agaggaggaa g                                               21

<210> SEQ ID NO 113
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 113 gcagggtgg cgaggaggaa g                                               21

<210> SEQ ID NO 114
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 114
ctgaggggtg ctccccggcc t                                              21

<210> SEQ ID NO 115
<211> LENGTH: 21
<212> TYPE: DNA
```

```
<213> ORGANISM: Artificial Sequence
<220> FEATURE:
<223> OTHER INFORMATION: Synthetic Polynucleotide

<400> SEQUENCE: 115
ctgaggggtg ttccccggcc t                                              21

<210> SEQ ID NO 116
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 116
ccttacagca acgtgctggg a                                              21

<210> SEQ ID NO 117
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 117
ccttacagca gcgtgctggg a                                              21

<210> SEQ ID NO 118
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 118
agagcaggac gctggaaccc a                                              21

<210> SEQ ID NO 119
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 119
agagcaggac tctggaaccc a                                              21

<210> SEQ ID NO 120
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 120
agagggccaa cgcataggaa g                                              21

<210> SEQ ID NO 121
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 121
agagggccaa tgcataggaa g                                              21
```

```
<210> SEQ ID NO 122
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 122
tctctctaac cttgcttcct t                                              21

<210> SEQ ID NO 123
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 123
tctctctaac tttgcttcct t                                              21
```

ANTISENSE OLIGONUCLEOTIDES TO RESTORE DYSFERLIN PROTEIN EXPRESSION IN DYSFERLINOPATHY PATIENT CELLS

RELATED APPLICATION

This application is a national stage filing under 35 U.S.C. § 371 of international PCT application, PCT/US2019/036045, filed Jun. 7, 2019, which claims priority under 35 U.S.C. § 119(e) to U.S. provisional patent application, U.S. Ser. No. 62/682,681, filed Jun. 8, 2018, the entire contents of each of which are incorporated herein by reference.

REFERENCE TO AN ELECTRONIC SEQUENCE LISTING

The contents of the electronic sequence listing (U012070105US01-SEQ-KZM.txt; Size: 25,468 bytes; and Date of Creation: Dec. 7, 2020) is herein incorporated by reference in its entirety.

BACKGROUND OF INVENTION

Dysferlin is a large transmembrane protein that functions in critical processes of membrane repair and vesicle fusion. Dysferlin-deficiency due to mutations in the dysferlin gene leads to muscular dystrophy (Miyoshi myopathy (MM), limb girdle muscular dystrophy type 2B (LGMD2B), distal myopathy with anterior tibial onset (DMAT)), typically with early adult onset. At least 416 pathogenic dysferlin mutations are known, but for approximately 17% of patients, one or both of the pathogenic variants remain undefined following standard exon sequencing methods that interrogate exons and nearby flanking intronic regions but not the majority of intronic regions.

Antisense oligonucleotides (AONs) are short nucleic acids or modified nucleic acids that have the potential to modify the expression of specific genes based on complementarity to regions of those genes, either within the protein coding region or in regulatory regions necessary for expression. AONs have thus been recognized as potential therapeutic agents to treat genetic disorders, possibly providing a means to modify the expression of disease causing mutant genes. AON reagents are currently in clinical use to treat Duchenne muscular dystrophy, a lethal X-linked neuromuscular disease affecting young boys that is caused by dystrophin deficiency that currently has no cure.

SUMMARY

The disclosure relates, in some aspects, to compositions and methods for utilizing antisense nucleic acids to alter the splicing of pre-messenger RNA (pre-mRNA) transcribed from a DYSF gene in a cell, wherein the DYSF gene contains a pseudoexon inserted between exons 50 and 51. In some embodiments, methods described by the disclosure are useful to diagnose and/or treat muscular dystrophies, such as Miyoshi myopathy or limb girdle muscular dystrophy type 2B, which result from abnormal expression of the DYSF gene.

In some aspects the disclosure provides a method of modulating splicing in a cell which contains a DYSF gene comprising a c.5668-824(C>T) mutation. The method comprises delivering to the cell an antisense nucleic acid that targets a prem-RNA such that exons 50 and 51 of the pre-mRNA are spliced together without an intervening pseudoexon. In some embodiments, a cell is heterozygous for the c.5668-824(C>T) point mutation, and comprises a second DYSF gene encodes a wild-type DYSF protein. In some embodiments, a second DYSF gene comprises a mutation that causes a premature stop codon. In some embodiments, a premature stop codon is within a C2G domain of DYSF protein. In some embodiments a second DYSF gene is a human DYSF gene, wherein the mutation that causes the premature stop codon is a c.3444_3445delTGinsAA mutation.

In some embodiments, a cell is in vitro, while in other embodiments, a cell is in vivo. In some embodiments, a cell is a non-human cell engineered to contain the DYSF gene comprising the c.5668-824(C>T) mutation. In some embodiments, a cell is a human cell engineered to contain the DYSF gene comprising the c.5668-824(C>T) mutation. In some embodiments, a human cell is from a subject having a muscular dystrophy. In some embodiments, a muscular dystrophy is of the Miyoshi myopathy-type, limb girdle muscular dystrophy type 2B (LGMB2B), or other muscular dystrophy caused by abnormal expression of the DYSF gene.

In some embodiments, an antisense nucleic acid is an oligonucleotide of 10 to 25 nucleotides in length comprising a region of complementarity that is complementary with at least 8 contiguous nucleotides of a sequence within a region between exons 50 and 51 encoded by a DYSF gene. In some embodiments, an oligonucleotide comprises a sequence of AON1 to AON20 as in Tables 5 and 6. In some embodiments, an AON is chemically modified (e.g., contains one or more 2'-O-methyl-modified nucleobases and/or one or more phosphorothioate linkages). In some embodiments, an antisense nucleic acid is expressed from a transgene, optionally wherein the transgene is delivered to the cell using a viral vector. In some embodiments, a viral vector is a recombinant AAV (rAAV) vector.

In some aspects, the disclosure provides a method of altering RNA splicing in a subject. In some embodiments, the method comprises administering to a subject an antisense nucleic acid that targets a pre-mRNA encoded by a DYSF gene and alters splicing of the pre-mRNA such that exons 50 and 51 of the RNA are spliced together without an intervening pseudoexon. In some embodiments, the human DYSF gene comprises a c.5668-824(C>T). In some aspects, methods described herein include a step of detecting that the subject has the human DYSF gene which comprises a c.5668-824(C>T) mutation prior to administering the antisense nucleic acid. In some embodiments, a human DYSF gene is detected using a hybridization assay that discriminates between the presence of a cytosine and a thymidine at position c.5668-824(C>T) of the human DYSF gene. In further embodiments, the hybridization assay is a polymerase chain reaction (PCR) assay, wherein the PCR assay comprises using a primer that is at least partially complementary with a nucleic acid having a sequence as set forth in SEQ ID NO: 103 or a complementary sequence thereof.

In some embodiments, an antisense nucleic acid is an oligonucleotide (e.g., a synthetic oligonucleotide) of 10 to 25 nucleotides in length comprising a region of complementarity that is complementary with at least 8 contiguous nucleotides of a sequence within a region between exons 50 and 51 encoded by a DYSF gene. In some embodiments, an oligonucleotide comprises a sequence of AON1 to AON20 as in Tables 5 and 6. In some embodiments, an antisense nucleic acid is expressed from a transgene, optionally wherein the transgene is delivered to the cell using a viral vector. In still further embodiments, a viral vector is a recombinant AAV vector.

In some aspects, the disclosure provides an oligonucleotide of 10 to 25 nucleotides in length comprising a region of complementarity that is complementary with at least 8 contiguous nucleotides of a sequence within a region between exons 50 and 51 encoded by a DYSF gene. In some embodiments, the oligonucleotides comprise at least one modified nucleotide or at least one modified internucleotide linkage. In some embodiments, the human DYSF gene comprises a c.5668-824(C>T). In further embodiments, the region of complementarity is complementary with at least 8 nucleotides of a sequence as set forth as SEQ ID NO: 103. In other embodiments, the region of complementarity is complementary with at least 8 nucleotides of a sequence as set forth as SEQ ID NO: 104 or 105.

In some embodiments, a region of complementarity is complementary with an exonic splice enhancer sequence. In some embodiments, a region of complementarity is complementary with a splice donor motif (e.g., of a DYSF gene). In some embodiments, a region of complementarity is complementary with a splice acceptor motif (e.g., of a DYSF gene). In some embodiments, a region of complementarity is complementary with a lariat branch point (e.g., of a DYSF gene).

In some embodiments, a human DYSF gene comprises a mutation that results in an in-frame pseudoexon between exons 50 and 51. In other embodiments, an oligonucleotide, when present in a cell that contains the human DYSF gene, alters splicing of a pre-mRNA expressed from the human DYSF gene such that the pseudoexon is not incorporated between exons 50 and 51. In some embodiments, an oligonucleotide comprises at least one modified nucleotide, optionally wherein the at least one modified nucleotide is a 2'-modified nucleotide. In some embodiments, the 2'-modified nucleotide is a 2'-deoxy, 2'-fluoro, 2'-O-methyl, 2'-O-methoxyethyl, 2'-amino and 2'-aminoalkoxy modified nucleotides. In other embodiments, the 2'-modified nucleotide comprises a 2'-O-4'C methylene bridge. In some embodiments, an oligonucleotide is fully 2'-O-methyl-modified (e.g., each nucleotide base of the oligonucleotide is 2'-O-methyl-modified).

In some embodiments, an oligonucleotide comprises at least one modified internucleotide linkage. In some embodiments, a modified linkage is a phosphorothioate modified linkage. In some embodiments, an oligonucleotide is fully phosphorothioate modified (e.g., all linkages of the oligonucleotide are phosphorothioate). In some embodiments, an oligonucleotide is fully 2-O-methyl and fully phosphorothioate modified.

In some embodiments, an oligonucleotide is a morpholino (or modified morpholino, e.g. peptide conjugated morpholino, phosphorodiamidate morpholino, etc.). In other embodiments, the oligonucleotide comprises alternating LNA and RNA nucleotides, LNA and DNA nucleotides, or RNA and DNA nucleotides.

In still other embodiments, an oligonucleotide, when present in a cell that contains the human DYSF gene, is capable of hybridizing with RNA expressed from the human DYSF gene without inducing cleavage of the RNA by an RNAse. In some embodiments, the disclosure provides a composition comprising an antisense oligonucleotides further comprising a carrier, for example a pharmaceutically-acceptable carrier.

In some aspects, the disclosure provides a preparation of oligonucleotides, wherein at least 95% of the oligonucleotides are 10 to 25 nucleotides in length and comprise a region of complementarity that is complementary with at least 8 nucleotides of a sequence within a region between exons 50 and 51 encoded by a human DYSF gene. In some embodiments, the region of complementarity is complementary with an exonic splice enhancer sequence. In some embodiments, the region of complementarity is complementary with a splice donor motif. In some embodiments, the region of complementarity is complementary with a splice acceptor motif. In some embodiments, the region of complementarity is complementary with a lariat branch point. In some embodiments of a preparation, a human DYSF gene comprises a mutation that results in an in-frame pseudoexon between exons 50 and 51. In some embodiments, the oligonucleotide, when present in a cell that contains the human DYSF gene, alters splicing of an RNA expressed from the human DYSF gene such that the pseudoexon is not incorporated between exons 50 and 51. In some embodiments of the preparation, the oligonucleotides are lyophilized. In some embodiments, at least 95% of the oligonucleotides are identical. In some embodiments, the disclosure provides a container housing the preparation of oligonucleotides as described above.

In some aspects, the disclosure provides one or more (e.g., pairs) of PCR primers having sequences selected from the primer sequences set forth in Table 3. In some embodiments, the disclosure provides a composition comprising the pair of PCR primers and a template comprising at least a portion of a human DYSF gene.

In some aspects, the disclosure provides an expression construct encoding an antisense nucleic acid having a region of complementarity that is complementary with a sequence between exons 50 and 51 encoded by a human DYSF gene. In some embodiments, the human DYSF gene comprises a c.5668-824(C>T) mutation. In some embodiments of the expression construct, the region of complementarity is complementary with at least 8 contiguous nucleotides of a sequence as set forth as SEQ ID NO: 103, 104, or 105. In some embodiments of the expression construct, the region of complementarity comprises a sequence complementary with an exonic splice enhancer sequence. In some embodiments, the region of complementarity comprises a sequence complementary with a splice donor motif. In some embodiments, the region of complementarity comprises a sequence complementary with a splice acceptor motif. In some embodiments of the expression construct, the region of complementarity comprises a sequence complementary with a lariat branch point. In some embodiments, the antisense nucleic acid expressed from the expression construct vector, when present in a cell that contains the human DYSF gene, alters splicing of a prem-RNA expressed from the human DYSF gene such that the pseudoexon is not incorporated between exons 50 and 51. In some embodiments, the disclosure provides a recombinant AAV comprising an expression construct as described herein (e.g., an expression construct engineered to express an oligonucleotide, such as an antisense oligonucleotide, as described by the disclosure).

In some aspects, the disclosure provides an engineered cell comprising an exogenous human DYSF gene having a c.5668-824(C>T) mutation, wherein the cell expresses a pre-mRNA from the exogenous DYSF gene containing a pseudoexon between exons 50 and 51. In some embodiments, the engineered cell is not of a human origin. In other embodiments, the engineered cell is of a human origin. In other embodiments, the disclosure provides a composition comprising cells containing a human DYSF gene having a c.5668-824(C>T) mutation and an artificial cell culture medium. In other embodiments, the disclosure provides a tissue culture system comprising a composition further comprising oligonucleotides as described above.

BRIEF DESCRIPTION OF DRAWINGS

FIG. 2A shows cDNA sequencing in which patients P1 and P2 have a 180 nucleotide insertion at the junction of exons 50 and 51, revealing the inclusion of a novel pseudoexon, PE50.1, splicing into the coding sequence. PE50.1 encodes 46 additional amino acids followed by a stop codon. FIG. 2B shows that DYSF intron 50i genomic DNA sequencing showed patients are heterozygous for a point mutation (c.57680824 C>T) (asterisk *) that creates a novel splice donor consensus site at the 3' end of the PE50.1 sequence. Both normal and mutant PE50.1-containint mRNA are expressed through alternative splicing of the DYSF transcripts. The mRNA structure within DYSF exon 50-intron 50i-exon 51 and the site of the 50i mutations is shown (insert, upper right), along with the normal and mutant splicing patterns. Numbers along the RNA indicate the size of each element in base pairs. FIG. 2C show the normal and mutant DYSF mRNA splice products and proteins in the region of exons 40-55. PE50.1 results in a 46 amino acid insertion and premature translation termination within the C2G domain and loss of the C-terminal transmembrane (TM) domain, both of which are required for dysferlin function. The predicted truncated protein would be 1935 amino acids rather than the normal 2081 amino acids.

FIG. 3A show pre-mRNA DYSF transcript and AON1, AON2, and AON3 (Table 5), which target potential exonic splicing enhancers in PE50.1 as shown. The primers in exon 50 (SEQ ID NO: 31) and 51 (SEQ ID NO: 30) amplify cDNAs to distinguish normal mRNA transcripts (88 base pair product containing exon 50+51) from mutant PE50.1 transcripts (268 base pair product containing exon 50+PE50.1+51). FIG. 3B shows RT-PCR analysis of mRNA splicing. Patient iFDM cells treated with AON1, AON2, and AON3 (duplicate cultures for each) expressed reduced amounts of PE50.1 mutant mRNA and higher normal DYSF mRNA compared with a non-specific scrambled (SCR) AON-treated, TE-treated, or no treatment cells. iFDM cells were allowed to differentiate in differential media (DM) for 6 days, then treated with AONs in DM for an additional 2 days, wherein (–RT) is no reverse transcriptase, H$_2$O is no RNA used in RT reactions.

FIG. 4A shows Western blots after 7 days of AON3 treatment (4 days after AON removal), where there was a dramatic increase in DYSF protein expression compared with control cells. GAPDH expression served as a control for protein loading (5 μg protein/lane). Protein levels in normal control iFDM cultures are not affected by AON treatments. FIG. 4B shows the quantitation of DYSF protein expressed in FIG. 4A, normalized to GAPDH levels and shown relative to normal cells treated with TE. The mean relative DYSF expression in patient cells was significantly higher in both AON2- and AON3-treated cells compared with SCR- or TE-treated controls (p<0.05, one-way ANOVA, Tukey's Multiple Comparison Test).

DETAILED DESCRIPTION

Aspects of the disclosure relate to methods for altering RNA splicing in a subject. In some embodiments, the disclosure provides compositions and methods for modulating splicing in a cell that contains a DYSF gene with a mutation that results in a pseudoexon between exons 50 and 51 which results in defects in dysferlin protein expression. There are a number of specific features of the dysferlin protein that contribute to its function and interaction with other proteins. Dysferlin has seven Ca$^{+2}$-sensitive phospholipid binding C2 domains (C2A to C2G) which vary in phospholipid binding characteristics, relative importance for dysferlin dimerization and membrane interaction but collectively may place a role in altering the structure or curvature of lipid bilayers facilitating membrane fusion and interaction with other membrane associated proteins. Dysferlin interacts with numerous proteins which function in membrane trafficking and fusion including caveolin-3, annexins, affixin, calpain-3, and AHNAK. Thus, dysferlin plays an important role in sarcolemma repair following membrane damage, as well as vesicle trafficking, membrane turnover, and T-tubule formation and stability.

A novel mutation was previously identified in the dysferlin gene (DYSF) that causes either Miyoshi myopathy or limb girdle muscular dystrophy type 2B (LGMB2B) due to the lack of normal dysferlin protein levels in patients' muscles (U.S. Ser. No. 15/316,027, the contents of which are incorporated herein by reference). This mutation is within intron 44 of the dysferlin gene and leads to incorporation of an extra segment of protein coding sequence derived from sequences within intron 44 (pseudoexon 44.1 (PE44.1)).

Inclusion of PE44.1 results in disruption of the normal dysferlin protein sequence by the insertion of additional amino acids.

Figure 1:
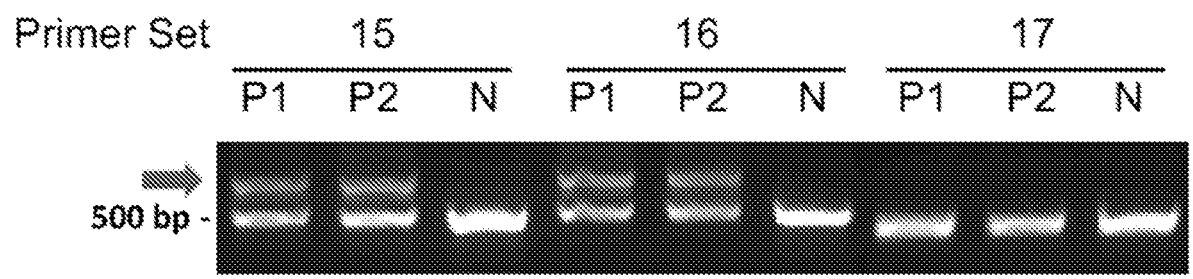
FIG. 1 shows the identification of the DYSF intron 50i mutation. RT-PCR of differentiated inducible fibroblast-derived myogenic (iFDM) cDNA from two patients (P1 (JF196), P2 (JF23)) shows novel amplicons (arrow) in patient samples that are not in a normal control sample (N). The amplicons were produced using two primer sets (SEQ ID NOs: 29 & 30, 31 & 32), whose amplicons overlap, but not with any other sets (e.g. SEQ ID NOs: 33 & 34), demonstrating additional sequence within patient cDNA in this region. Each PCR product was sequenced to identify the inserted sequence.

This disclosure describes a second pathogenic deep mutation in DYSF intron 50i that leads to inclusion of pseudo-exon 50.1 (PE50.1) (FIG. 1). This mutation was found in patients from 17 families, making it one of the more prevalent known DYSF mutations. Other aspects of the disclosure provide methods of administering antisense oligonucleotides (AONs) to alter pre-mRNA splicing of the DYSF gene such that the pseudoexon (PE50.1) is not incorporated between exons 50 and 51 significantly restoring normal RNA expression and dysferlin protein levels.

Antisense Oligonucleotides

As used herein, the term, "antisense nucleic acid," refers to a nucleic acid that has sequence complementarity to a target sequence and is specifically hybridizable, e.g., under stringent conditions, with a nucleic acid having the target sequence. An antisense nucleic acid is specifically hybridizable when binding of the antisense nucleic acid to the target nucleic acid is sufficient to produce complementary based pairing between the antisense nucleic acid and the target nucleic acid, and there is a sufficient degree of complementarity to avoid non-specific binding of the antisense nucleic acid to non-target nucleic acid under conditions in which specific binding is desired, e.g., under physiological conditions in the case of in vivo assays or therapeutic treatment, and in the case of in vitro assays, under conditions in which the assays are performed.

In some embodiments, an antisense nucleic acid is used that has a region of complementarity that is perfectly complementary to a portion of a target nucleic acid (e.g., target RNA). However, it should be appreciated that in some embodiments, an antisense nucleic acid may be used that has less than 100% sequence complementarity with a target nucleic acid. An antisense nucleic acid oligonucleotide may comprise a region of complementarity that is complementary with sequence as set forth in SEQ ID NO: 103, 104, or 105. The region of complementarity of the antisense nucleic acid may be complementary with at least 6, e.g., at least 7, at least 8, at least 9, at least 10, at least 15 or more consecutive nucleotides of a target nucleic acid. In addition, to minimize the likelihood of off-target effects, an antisense nucleic acid may be designed to ensure that it does not have a sequence (e.g., of 5 or more consecutive nucleotides) that is complementary with an off-target nucleic acid.

Complementary refers to the capacity for precise pairing between two nucleotides. For example, if a nucleotide at a certain position of an antisense nucleic acid is capable of hydrogen bonding with a nucleotide at the corresponding position of a target nucleic acid (e.g., target RNA), then the antisense nucleic acid and target nucleic acid are considered to be complementary to each other at that position. The antisense nucleic acid and target nucleic acid are complementary to each other when a sufficient number of corresponding positions in each molecule are occupied by nucleotides that can hydrogen bond with each other through their bases. Thus, "complementary" is a term that is used to indicate a sufficient degree of complementarity or precise pairing such that stable and specific binding occurs between the antisense nucleic acid and target nucleic acid. However, it should be appreciated that 100% complementarity is not required. For example, in some embodiments, an antisense nucleic acid (e.g., an oligonucleotide) may be at least 80% complementary to (e.g., at least 85%, 90%, 91%, 92%, 93%, 940%, 95%, 96%, 97%, 98%, 99% or 100% complementary to) the consecutive nucleotides of a target nucleic acid.

Thus, it is understood in the art that a complementary nucleotide sequence need not be 100% complementary to that of its target to be specifically hybridizable. In some embodiments, a complementary nucleic acid sequence for purposes of the present disclosure is specifically hybridizable when binding of the sequence to the target nucleic acid produces the desired alterations in splicing to occur and there is a sufficient degree of complementarity to avoid non-specific binding to non-target nucleic acids under conditions in which avoidance of non-specific binding is desired, e.g., under physiological conditions in the case of in vivo assays or therapeutic treatment, and in the case of in vitro assays, under conditions in which the assays are performed under suitable conditions of stringency.

Sequence identity, including determination of sequence complementarity for nucleic acid sequences, may be determined by sequence comparison and alignment algorithms known in the art. To determine the percent identity of two nucleic acid sequences, the sequences are aligned for optimal comparison purposes (e.g., gaps can be introduced in the first sequence or second sequence for optimal alignment). The nucleotides at corresponding nucleotide positions are then compared. When a position in the first sequence is occupied by the same residue as the corresponding position in the second sequence, then the molecules are identical at that position. In some embodiments, the percent identity between the two sequences is a function of the number of identical positions shared by the sequences (e.g., % homology=# of identical positions/total # of positions×100), optionally penalizing the score for the number of gaps introduced and/or length of gaps introduced.

In some embodiments, an antisense nucleic acid is an antisense oligonucleotide (AON), which may be referred to simply as an oligonucleotide. For example, in some embodiments, oligonucleotides are provided that comprise a region of complementarity that is complementary with at least 8, at least 9, at least 10, at least 11, at least 12, at least 13, at least 14, at least 15 or more contiguous nucleotides of a sequence within a region between exons 50 and 51 encoded by a human DYSF gene. Such oligonucleotides are useful for modulating splicing of dysferlin and prevent incorporation of a pseudoexon between exons 50 and 51. In some embodiments, an antisense nucleic acid is an antisense oligonucleotide (AON) recited in Table 5 or Table 6.

In some embodiments, oligonucleotides of the disclosure have a length in a range of 5 to 40 nucleotides, 5 to 30 nucleotides, 10 to 30 nucleotides, 10 to 25 nucleotides, or 15 to 25 nucleotides. In some embodiments of the disclosure, oligonucleotides have a length of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more. In some embodiments, the oligonucleotide comprises a region of complementarity that is complementary with a region within 5, 10, 15, 25, 50, 100 or 200 nucleotides of a c.5668-824 (C>T) mutation in a human DYSF gene. In some embodiments, the oligonucleotide comprises a region of complementarity that is complementary with at least 8 contiguous nucleotides of a sequence as set forth as SEQ ID NO: 103. In some embodiments, the oligonucleotide comprises a region of complementarity that is complementary with at least 8 contiguous nucleotides of a sequence as set forth as SEQ ID NO: 104 or 105. The region of complementarity may be complementary with an exonic splice enhancer or inhibitor sequence, a splice donor motif, a splice acceptor motif or a lariat branch point encoded by a human DYSF gene (e.g., within a region spanning from exon 50 to exon 51).

In some embodiments, antisense nucleic acids (e.g., oligonucleotides) are provided in a homogeneous preparation, e.g., in which at least 85%, at least 90%, at least 95%, or at least 99% of the oligonucleotides are identical. For example, in some embodiments, homogeneous preparations of oligonucleotides are provided in which at least 85%, at least 90%, at least 95%, or at least 99% of the oligonucleotides in the preparation are 10 to 25 nucleotides in length and comprise a region of complementarity that is complementary with at least 8 contiguous nucleotides of a sequence within a region between exons 50 and 51 encoded by a human DYSF gene.

Antisense nucleic acids of the disclosure may be modified to achieve one or more desired properties, such as, for example, improved cellular uptake, improved stability, reduced immunogenicity, improved potency, improved target hybridization, susceptibility to RNAse cleavage, etc. In some embodiments, an antisense nucleic acid is modified such that when present in a cell that contains a human DYSF gene, it is capable of hybridizing with RNA expressed from the human DYSF gene without inducing cleavage of the RNA by an RNase. Antisense nucleic acids can be modified at a base moiety, sugar moiety and/or phosphate backbone. Accordingly, antisense nucleic acids may have one or more modified nucleotides (e.g., a nucleotide analog) and/or one or more backbone modifications (e.g., a modified internucleotide linkage). Antisense nucleic acids may have a combination of modified and unmodified nucleotides. Antisense nucleic acids may also have a combination of modified and unmodified internucleotide linkages.

Antisense nucleic acids may include ribonucleotides, deoxyribonucleotides, and combinations thereof. Examples of modified nucleotides which can be used in antisense nucleic acids include, for example, 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, and 2,6-diaminopurine.

In some embodiments, a modified nucleotide is a 2'-modified nucleotide. For example, the 2'-modified nucleotide may be a 2'-deoxy, 2'-fluoro, 2'-O-methyl, 2'-O-methoxyethyl, 2'-amino and 2'-aminoalkoxy modified nucleotides. In some embodiments, the 2'-modified nucleotide comprises a 2'-O-4'-C methylene bridge, such as a locked nucleic acid (LNA) nucleotide. In some embodiments of a 2' modified nucleotide the 2'-hydroxyl group is linked to the 3' or 4' carbon atom of the sugar ring thereby forming a bicyclic sugar moiety. In such embodiments, the linkage may be a methelyne (—CH2-)$_n$ group bridging the 2' oxygen atom and the 3' or 4' carbon atom wherein n is 1 or 2.

Antisense nucleic acids may include combinations of LNA nucleotides and unmodified nucleotides. Antisense nucleic acids may include combinations LNA and RNA nucleotides. Antisense nucleic acids may include combinations LNA and DNA nucleotides. A further preferred oligonucleotide modification includes Locked Nucleic Acids (LNAs) in which the 2'-hydroxyl group is linked to the 3' or 4' carbon atom of the sugar ring thereby forming a bicyclic sugar moiety.

Antisense nucleotide acids may also include nucleobase-modified nucleotides, e.g., nucleotides containing a non-naturally occurring nucleobase instead of a naturally occurring nucleobase. Bases may be modified to block the activity of adenosine deaminase, for example. Examples of modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

Within antisense nucleic acids (e.g., oligonucleotides) of the disclosures, as few as one and as many as all nucleotides can be modified. For example, an oligonucleotide (e.g., an oligonucleotide of 20 nucleotides in length) may contain 1, 2, 3, 4, 5, 6, 7, 8, 9, 10, 11, 12, 13, 14, 15, 16, 17, 18, 19 or 20 modified nucleotides. In some embodiments, a modified oligonucleotide will contain as few modified nucleotides as are necessary to achieve a desired level of in vivo stability and/or bioaccessibility or other desired property.

Certain antisense nucleic acids may include nonionic DNA analogs, such as alkyl- and aryl-phosphates (in which the charged phosphonate oxygen is replaced by an alkyl or aryl group), phosphodiester and alkylphosphotriesters, in which the charged oxygen moiety is alkylated. Nucleic acids which contain a diol, such as tetraethyleneglycol or hexaethyleneglycol, at either or both termini have also been shown to be substantially resistant to nuclease degradation and may be used herein. In some embodiments, antisense nucleic acids may include at least one lipophilic substituted nucleotide analog and/or a pyrimidine-purine dinucleotide.

In some embodiments, antisense nucleic acids (e.g., oligonucleotides) may have one or two accessible 5' ends. It is possible to create modified oligonucleotides having two such 5' ends, for instance, by attaching two oligonucleotides through a 3'-3' linkage to generate an oligonucleotide having one or two accessible 5' ends. The 3'3'-linkage may be a phosphodiester, phosphorothioate or any other modified internucleoside bridge. Additionally, 3'3'-linked oligonucleotides where the linkage between the 3' terminal nucleosides is not a phosphodiester, phosphorothioate or other modified bridge, can be prepared using an additional spacer, such as tri- or tetra-ethylenglycol phosphate moiety.

A phosphodiester internucleotide linkage of an antisense nucleic acid can be replaced with a modified linkage. The modified linkage may be selected from, for example, phosphorothioate, phosphorodithioate, NR1R2-phosphoramidate, boranophosphate, α-hydroxybenzyl phosphonate, phosphate-(C1-C21)-O-alkyl ester, phosphate-[(C6-C12) aryl-(C1-C21)-O-alkyl]ester, (C1-C8)alkylphosphonate and/or (C6-C12)arylphosphonate bridges, and (C7-C12)-α-hydroxymethyl-aryl.

A phosphate backbone of the antisense nucleic acid can be modified to generate peptide nucleic acid molecules. As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols, for example.

Antisense nucleic acids can also be formulated as morpholino oligonucleotides. In such embodiments, the riboside moiety of each subunit of an oligonucleotide of the oligonucleotide reagent is converted to a morpholine moiety. Morpholinos may also be modified, e.g. as a peptide conjugated morpholino, a phosphorodiamidate morpholino, etc.

In other embodiments, the antisense nucleic acid (e.g., oligonucleotide) can be linked to functional groups such as peptides (e.g., for targeting host cell receptors in vivo), or agents facilitating transport across the cell membrane or the blood-brain barrier. Oligonucleotide reagents of the disclosure also may be modified with chemical moieties (e.g., cholesterol) that improve the in vivo pharmacological properties of the oligonucleotide reagents.

Dysferlinopathies

Dysferlinopathy is a degenerative muscle disease cause by insufficient expression of dysferlin protein in skeletal muscles. This is a recessively-inherited disorder with onset in late teens to early adulthood as muscle weakness due to muscle degeneration, which progressively worsens, typically leading to significant loss of mobility. There is currently no cure for dysferlinopathy, and treatment is currently palliative. Clinical trials have recently begun to evaluate a virally-mediated gene replacement strategy to restore dysferlin expression.

Dysferlin is a member of the ferlin family of $Ca^{+2}$-dependent phospholipid-binding proteins. Dysferlin is a large (237 kilodaltons, kDa) transmembrane protein critical in membrane repair, vesicle trafficking, and T-tubule structure. The dysferlin protein is derived from a ~6.2 kb transcript assembled from up to 55 exons. There are 14 known human isoforms of dysferlin, generated by altered exon splicing and the use of two alternate promoters, with isoform 8 being the predominant form in muscle. In addition to skeletal muscle, dysferlin is expressed in other tissues, and dysferlin-deficiency has been associated with immune cell migration changes such as increased motility and phagocytosis by blood monocytes. The dysferlin expression level in blood monocytes can be used as a diagnostic tool for dysferlinopathy.

At least 416 different pathogenic dysferlin variants are listed in the Universal Mutation Database (UMD-DYSF, umd.be/DYSF/), most lying within one of the 55 exons that are spliced together to form isoform 8 that is critical for muscle function. For approximately 17% of patients, a complete understanding of the genetic lesions underlying the disease is lacking; at least one of the pathogenic mutations has not been identified. It is likely that these mutations lie within dysferlin introns or areas other than exons that regulate dysferlin expression. These gene regions are not examined by standard exonic screening methods.

A pathogenic variant deep within dysferlin intron 44 (44i) (c.4866+1249G>T) in dysferlinopathy patients was previously identified (see WO 2015/187825A2, the contents of which are incorporated herein by reference). This intronic variant induces alternate splicing of the dysferlin transcript, allowing the inclusion of a 177 bp pseudoexon (PE44.1) within the mature transcript, resulting in an in-frame insertion of 59 amino acids within the C2F domain of the dysferlin protein.

The disclosure is based, in part, on the identification of a new deep intronic mutation located between dysferlin exons 50 and 51. This intronic variant induces alternative splicing of the dysferlin transcript, allowing the inclusion of a 180 bp pseudoexon 51 (also referred to as PE50.1) within the mature transcript, resulting in an in-frame insertion of 46 amino acids within the C2G region of the dysferlin protein.

In some embodiments, at least 14 variants (e.g., isoforms) of DYSF transcripts that arise from use of two separate promoters and/or alternate exon splicing events. In some embodiments, DYSF mRNA variant 8 (NM_003494.3) is used as a reference for RNA and cDNA analyses and/or as a context for specifying exon and intron numeric assignments and nomenclature.

A dysferlinopathy is a muscular dystrophy caused mutations in the dysferlin gene. Examples of dysferlinopathies included limb-girdle muscular dystrophy type 2B, Miyoshi myopathy, and distal anterior compartment myopathy. In limb-girdle muscular dystrophies, the muscles in the shoulder and pelvic girdle are most affected and early symptoms include difficulty running, climbing stairs, standing, and walking. In Myoshi myopathy, early symptoms are most pronounced in distal portions of the legs and as the disease worsens, progress through the thighs, gluteal muscles, forearms, and shoulder girdle muscles.

Treatment Methods

Aspects of the disclosure relate to methods of altering RNA splicing in a subject involving administering to the subject an antisense nucleic acid that targets a pre-messenger RNA encoded by a human DYSF gene and alters splicing of the pre-messenger RNA such that exons 50 and 51 of the RNA are spliced together without an intervening pseudoexon. In some embodiments, the subject is heterozygous a c.5668-824 (C>T) mutation in the DYSF gene. However, in some embodiments, the subject is homozygous a c.5668-824 (C>T) mutation in the DYSF gene. Often the subject has or is suspected of having muscular dystrophy (e.g., of the Miyoshi Myopathy-type) caused by abnormal expression of the dysferlin gene product and the methods are being implemented for purposes of treating the muscular dystrophy. Treating, in this case, includes improving dysferlin expression and/or ameliorating one or more symptoms of muscular dystrophy.

Any appropriate antisense nucleic acid disclosed herein may be administered. For example, the antisense nucleic acid may be an oligonucleotide (e.g., of 10 to 25 nucleotides in length) comprising a region of complementarity that is complementary with a sequence within a region between exons 50 and 51 encoded by a human DYSF gene. An antisense oligonucleotide may for example comprise a sequence of AON1 to AON20 as set forth in Tables 5 and 6.

In some embodiments, an antisense nucleic acid is expressed from a transgene, e.g., as an antisense RNA transcript. A transgene may be administered to a subject in a DNA expression construct that is engineered to express an antisense RNA transcript in a subject. A DNA expression construct may be administered directly or using a viral vector (e.g., a recombinant AAV (rAAV) vector) or other suitable vector. Viral vectors that have been used for gene therapy protocols include, but are not limited to, retroviruses, other RNA viruses such as poliovirus or Sindbis virus, adenovirus, adeno-associated virus (AAV), herpes viruses, SV 40, vaccinia, lentivirus and other DNA viruses.

Alternatively, a transgene may be express ex vivo and the resulting antisense RNA transcript may be administered directly to the subject.

As disclosed herein antisense nucleic acids (including DNA expression constructs that may be used to expressed them) may be administered by any suitable route. For use in therapy, an effective amount of the antisense nucleic acid (e.g. oligonucleotide) and/or other therapeutic agent can be administered to a subject by any mode that delivers the agent to the desired tissue, e.g., muscle tissue. In some embodiments, agents (e.g., antisense nucleic acids) are administered intramuscularly. Other suitable routes of administration include but are not limited to oral, parenteral, intravenous, intraperitoneal, intranasal, sublingual, intratracheal, inhalation, subcutaneous, ocular, vaginal, and rectal. Systemic routes include oral and parenteral. Several types of devices are regularly used for administration by inhalation. These types of devices include metered dose inhalers (MDI), breath-actuated MDI, dry powder inhaler (DPI), spacer/holding chambers in combination with MDI, and nebulizers.

For oral administration, the agents can be formulated readily by combining the active compound(s) with pharmaceutically acceptable carriers well known in the art. Such carriers enable the agents of the disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally oral formulations may also be formulated in saline or buffers for neutralizing internal acid conditions or may be administered without any carriers.

Pharmaceutical preparations that can be used orally include push fit capsules made of gelatin, as well as soft, sealed capsules made of gelatin and a plasticizer, such as glycerol or sorbitol. The push fit capsules can contain the active ingredients in admixture with filler such as lactose, binders such as starches, and/or lubricants such as talc or magnesium stearate and, optionally, stabilizers. In soft capsules, the active agents may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. Formulations for oral administration are typically in dosages suitable for such administration.

For buccal administration, the compositions may take the form of tablets or lozenges formulated in conventional manner.

For administration by inhalation, agents (e.g., antisense nucleic acids) for use according to the present disclosure may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The agents (e.g., antisense nucleic acids), when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of agents (e.g., antisense nucleic acids) in water-soluble form. Additionally, suspensions of agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the agents to allow for the preparation of highly concentrated solutions. Alternatively, agents (e.g., antisense nucleic acids) may be in powder form for constitution with a suitable vehicle, e.g., sterile pyrogen-free water, before use. Agents (e.g., antisense nucleic acids) may also be formulated in rectal or vaginal compositions such as suppositories or retention enemas, e.g., containing conventional suppository bases such as cocoa butter or other glycerides.

Other delivery systems can include time-release, delayed release or sustained release delivery systems. Such systems can avoid repeated administrations of the agents (e.g., antisense nucleic acids), increasing convenience to the subject and the physician. Many types of release delivery systems are available. They include polymer base systems such as poly(lactide glycolide), copolyoxalates, polycaprolactones, polyesteramides, polyorthoesters, polyhydroxybutyric acid, and polyanhydrides. Delivery systems also include non-polymer systems that are: lipids including sterols such as cholesterol, cholesterol esters and fatty acids or neutral fats such as mono, di, and tri glycerides; hydrogel release systems; silastic systems; peptide-based systems; wax coatings; compressed tablets using conventional binders and excipients; partially fused implants; and others disclosed herein.

Analytical Methods

In some aspects, the disclosure relates to the methods for detecting presence of a mutation causing an insertion in between exon 50 and exon 51 of the DYSF gene. In some embodiments, a clinical sample is obtained from a subject for the purpose of identifying a mutation. As used herein, a clinical sample refers to a specimen of biological matter obtained from a subject for the purpose of analysis or diagnosis. Non-limiting examples of clinical samples include blood, saliva, urine, feces, tissue, semen, cerebral spinal fluid, nucleic acids, epithelial cells, sweat, tears, hair and mucous.

In some embodiments, a clinical sample may be obtained from the blood of the patient. In some embodiments, a clinical sample may be obtained from the cells in the blood of a subject. In some embodiments, the cells may be blood cells. In some embodiments, a clinical sample may be obtained from the tissue of a subject. In some embodiments, the tissue of the subject is muscle tissue. In some embodiments, the muscle tissue comprises skeletal muscle. In some embodiments, the muscle tissue comprises smooth muscle. In some embodiments, the muscle tissue comprises cardiac tissue. In some embodiments the clinical sample is obtained from a tissue that is not a muscle tissue. In some embodiments the non-muscle tissue comprises mesenchymal cells.

In some embodiments, the tissue of the subject is skin tissue. In some embodiments, the non-muscle tissue comprises fibroblasts.

In some embodiments, a non-muscle tissue comprises stem cells, including, for example, embryonic stem cells, tissue stem cells, umbilical cord stem cells, mesenchymal stem cells, induced pluripotent stem cells, multipotent stem cells, totipotent stem cells, unipotent stem cells, progenitor cells, blastocysts, bone marrow stromal cells, hematopoietic stem cells, oligopotent stem cells, neural stem cells, and trophoblast stem cells.

In some embodiments, methods may involve genotyping a subject with respect to the human DYSF gene for purposes of selecting an appropriate treatment for the subject. For example, a subject may be administered an antisense nucleic acid disclosed herein if it is determined that the subject has a DYSF gene having a mutation that results an in-frame pseudoexon being coded for between exons 50 and 51 (e.g., a c.5668-824 (C>T) mutation.) Often the subject has or is suspected of having muscular dystrophy (e.g., of the Miyoshi Myopathy-type) caused by abnormal expression of the dysferlin gene product.

The genotype of the subject may be assessed using a hybridization assay that discriminates between the presence of a guanosine and a thymidine at position c.5668-824 of the human DYSF gene. An example of a suitable hybridization is a polymerase chain reaction (PCR) based allelic discrimination assay. A PCR based assay may be performed, for example, by using a primers that are at least partially complementary with a nucleic acid having a sequence as set forth in SEQ ID NO: 103, 104, or 105 or a complementary sequence thereof together with a suitable probe for detecting presence or absence of a particular mutation. In some embodiments, one or more PCR amplicons may be sequenced and the obtained sequence may be evaluated for purposes of detecting presence or absence of a particular mutation. In some embodiments, a pair of primers disclosed in Table 3 or 4 be used to amplify one or more regions of the DYSF gene for purposes of determining the sequence of the DYSF and/or detecting presence or absence of a particular mutation in the DYSF gene.

Cells

In some aspects, the present disclosure relates to the delivery of antisense nucleic acids (e.g. oligonucleotides) to a target cell. In some embodiments, the cell is of a subject having a DYSF gene containing a c.5668-824 (C>T) mutation. The cell may be heterozygous for the mutated gene or may be homozygous. The cell may have a second DYSF gene (a second allele of the gene) encoding a wild-type DYSF protein. The cell may have a second DYSF gene (a second allele of the gene) having a different mutation than the c.5668-824 (C>T) mutation. For example, the cell may contain a DYSF gene comprising a mutation that causes a premature stop codon (e.g., within a region encoding the C2D domain of DYSF protein). For example, the premature stop codon may be a c.3444_3445delTGinsAA mutation. The cell to which the antisense nucleic acid is delivered may be in vitro or in vivo.

In some embodiments, the cell is a mammalian cell. In some embodiments the mammalian cell is a human cell. The cell may be from a subject having a muscular dystrophy that is associated at least in part with the DYSF gene comprising the c.5668-824 (C>T) mutation. For example, the muscular dystrophy is of the Miyoshi Myopathy-type, or other muscular dystrophy caused by abnormal expression of the dysferlin gene product. In some embodiments, the cell is a myoblast or other muscle progenitor cell. In some embodiments, the cells are muscle cells. In some embodiments of the disclosure the muscle cells are striated (e.g. skeletal) muscle cells (e.g., myotubes). In some embodiments, the muscle cells are cardiac smooth muscle cells. In some embodiments, the muscle cells are smooth muscle cells. In some embodiments the cells are not muscle cells. In some embodiments, cells are of the brain, heart, kidneys, lungs, uterus, spleen, pancreas or muscle tissue of a subject. In some embodiments, the cell is a non-human cell (e.g., a non-human mammalian cell, e.g., a mouse cell). For example, the cell may be a non-human cell (e.g., a mouse cell) engineered to contain one or more copies of the human DYSF gene comprising the c.5668-824 (C>T) mutation.

Pharmaceutical Compositions

According to some aspects of the disclosure, compositions are provided that comprise an agent (e.g., an antisense nucleic acid (e.g., an oligonucleotides) or vector comprising the same) and a carrier. As used herein, the term, "carrier" refers to an organic or inorganic ingredient, natural or synthetic, with which the active ingredient is combined to facilitate an intended use. For example, pharmaceutical compositions are provided that comprise an antisense nucleic acid and a pharmaceutically-acceptable carrier. As used herein the term "pharmaceutically acceptable carrier" refers to a carrier that is suitable for pharmaceutical administration. The term pharmaceutically-acceptable carrier includes compatible solid or liquid fillers, diluents or encapsulating substances that are suitable for administration to a human or other vertebrate animal.

Components of pharmaceutical compositions also are capable of being commingled with the agents of the present disclosure, and with each other, in a manner such that there is no interaction that would substantially impair the desired pharmaceutical efficiency. Pharmaceutical compositions may include solvents, dispersion media, coatings, antibacterial and antifungal agents, isotonic and absorption delaying agents, and other suitable components compatible with pharmaceutical administration. Supplementary active agents can also be incorporated into the compositions. Active ingredients (e.g., oligonucleotides) may be admixed or compounded with any conventional, pharmaceutically acceptable carrier or excipient. Pharmaceutical compositions are generally sterile and prepared using aseptic technique. A sterile phosphate-buffered saline is one example of a pharmaceutically acceptable carrier. Other suitable carriers may be used. Pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Antisense nucleic acids may be administered per se (neat) or in the form of a pharmaceutically acceptable salt. When used in medicine the salts are generally pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The compositions may conveniently be presented in unit dosage form and may be prepared by any of the methods well known in the art of pharmacy. All methods include the step of bringing the agents into association with a carrier that constitutes one or more accessory ingredients. In general, the compositions are prepared by uniformly and intimately bringing the agents into association with a liquid carrier, a finely divided solid carrier, or both, and then, if necessary, shaping the product. Liquid dose units are vials or ampoules. Solid dose units are tablets, capsules and suppositories.

An effective amount, also referred to as a therapeutically effective amount, of an antisense nucleic acid (e.g. oligonucleotide) capable of modulating splicing in a cell in which the DYSF gene is expressed is an amount sufficient to ameliorate at least one adverse effect associated with expression, or reduced expression, of the gene in a cell or in an individual in need of such modulation. The therapeutically effective amount to be included in pharmaceutical compositions may be selected based upon several factors, e.g., the type, size and condition of the patient to be treated, the intended mode of administration, the capacity of the patient to incorporate the intended dosage form, etc.

In some cases, antisense nucleic acids may be prepared in a colloidal dispersion system. Colloidal dispersion systems include lipid-based systems including oil-in-water emulsions, micelles, mixed micelles, and liposomes. An example of a colloidal system that may be used in methods provided herein is a liposome. Liposomes are artificial membrane vessels that are useful for delivering antisense nucleic acids in vivo or in vitro. It has been shown that large unilamellar vesicles can encapsulate large macromolecules. Nucleic acids and other components (e.g., viral vectors) can be encapsulated within the aqueous interior and be delivered to cells in a biologically active form. Liposomes may be targeted to a particular tissue by coupling the liposome to a specific ligand such as a monoclonal antibody, sugar, glycolipid, or protein. Ligands which may be useful for targeting a liposome to, for example, a smooth muscle cell or skeletal muscle cell include, but are not limited to: intact or fragments of molecules that interact with muscle cell specific receptors and molecules, such as antibodies, which interact with the cell surface markers. Lipid formulations for transfection are commercially available from QIAGEN, for example, as EFFECTENE™ (a non-liposomal lipid with a special DNA condensing enhancer) and SUPERFECT™ (a dendrimeric technology). Liposomes are commercially available from Invitrogen, Life Technologies, for example, as LIPOFECTIN™, which is formed of cationic lipids such as N-[1-(2,3 dioleyloxy)-propyl]-N, N, N-trimethylammonium chloride (DOTMA) and dioleoyl phophotidylethanolamine (DOPE), as well as other lipid-based reagents including Lipofectamine and Oligofectamine. Certain cationic lipids, including in particular N-[1-(2,3 dioleoyloxy)-propyl]-N,N,N-trimethylammonium methyl-sulfate (DO-TAP), may be advantageous when combined with the antisense nucleic acids (e.g. oligonucleotides) analogs of the disclosure.

In one embodiment, antisense nucleic acids may be formulated with a biocompatible microparticle or implant that is suitable for implantation or administration to a recipient. Bioerodible implants may include a biodegradable polymeric matrix, for example, for containing an exogenous expression construct engineered to express an antisense nucleic acid under the control of an appropriate promoter. The polymeric matrix can be used to achieve sustained release of the therapeutic agent in the subject. A polymeric matrix may be in the form of a microparticle such as a microsphere, in which an antisense nucleic acid and/or other therapeutic agent is dispersed throughout a solid polymeric matrix, or a microcapsule, in which antisense nucleic acid and/or other therapeutic agent is stored in the core of a polymeric shell. Other forms of the polymeric matrix for containing a therapeutic agent include films, coatings, gels, implants, and stents. The matrix composition also can be selected not to degrade, but rather, to release by diffusion over an extended period of time. In some embodiments, antisense nucleic acids are administered to the subject via an implant while the other therapeutic agent is administered.

Both non-biodegradable and biodegradable polymeric matrices can be used to deliver antisense nucleic acids (e.g. oligonucleotides) and/or the other therapeutic agent to a subject. Biodegradable matrices are preferred. Such polymers may be natural or synthetic polymers. The polymer is selected based on the period of time over which release is desired, generally in the order of a few hours to a year or longer. Typically, release over a period ranging from between a few hours and three to twelve months may be used. A polymer may be in the form of a hydrogel, e.g., a hydrogel that can absorb up to about 90% of its weight in water and which is optionally cross-linked with multi-valent ions or other components, e.g., polymers.

Other exemplary compositions that can be used to facilitate uptake of a nucleic acid include calcium phosphate and other chemical mediators of intracellular transport, microinjection compositions, electroporation and homologous recombination compositions (e.g., for integrating a nucleic acid into a preselected location within the target cell chromosome).

In addition to the formulations described previously, the agents may also be formulated as a depot preparation. Such long-acting formulations may be formulated with suitable polymeric or hydrophobic materials (for example as an emulsion in an acceptable oil) or ion exchange resins, or as sparingly soluble derivatives, for example, as a sparingly soluble salt.

Other suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems.

Kits

Agents (e.g., antisense nucleic acids) described herein may, in some embodiments, be assembled into pharmaceutical or diagnostic or research kits to facilitate their use in therapeutic, diagnostic or research applications. A kit may include one or more containers housing the components and instructions for use. Specifically, such kits may include one or more agents (e.g., antisense nucleic acids) described herein, along with instructions describing the intended therapeutic application and the proper administration of these agents. In certain embodiments agents in a kit may be in a pharmaceutical formulation and dosage suitable for a particular application and for a method of administration of the agents.

The kit may be designed to facilitate use of the methods described herein by physicians and can take many forms. Each of the agents of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to a patient, such as a syringe, topical application devices, or IV needle tubing and bag.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

EXAMPLES

Example 1, Identification of a Deep Intronic Mutation in DYSF Intron 50i

Skin fibroblast cultures from sibling dysferlinopathy patients JF196 and JF23 were converted to myogenic iFDM cell lines and induced to differentiate into myotubes. RNA was then isolated and isolated by RT-PCR to determine the sequence of any dysferlin expressed in these cells. The dysferlin mRNA was analyzed using PCR primers that generated overlapping amplicons tiling through the entire mRNA. Two of the overlapping amplicon products from these patients were larger than products from normal iFDM cells, indicating an insertion of extra sequence within the dysferlin transcript in these patients (FIG. 1).

Figure 2A:
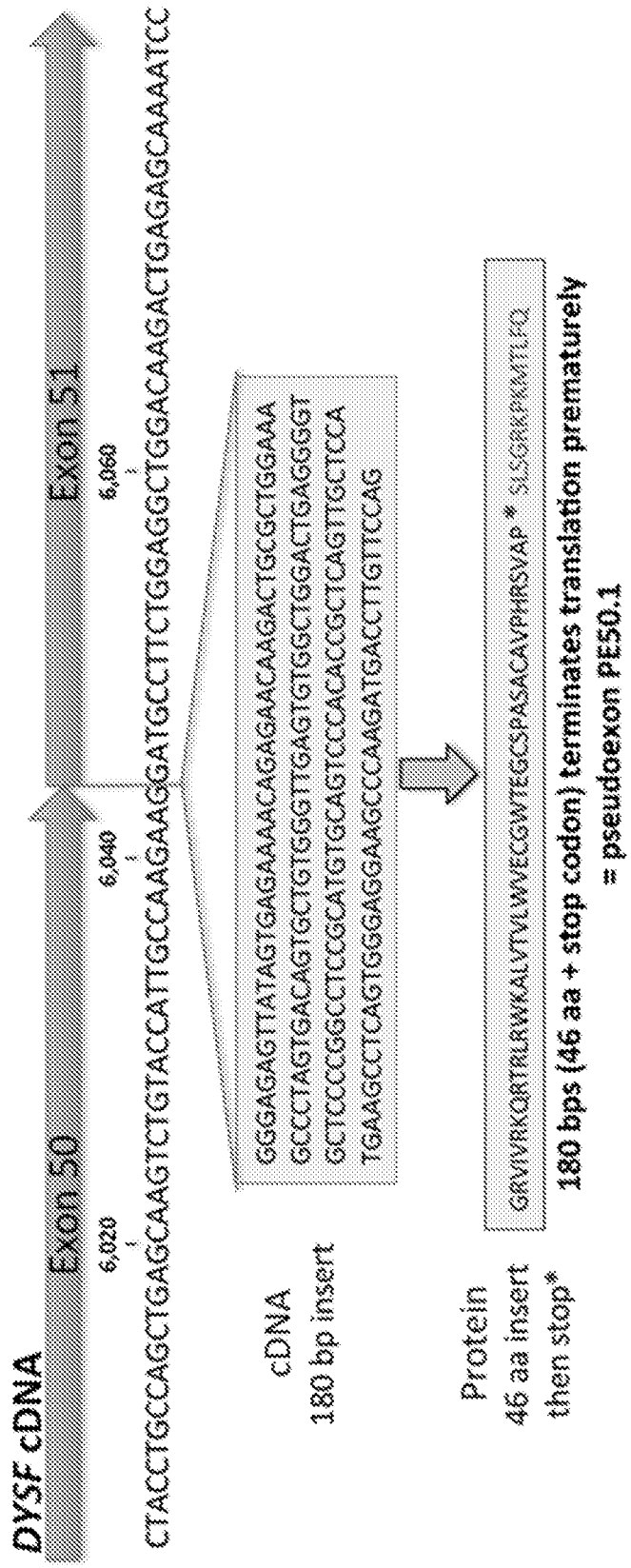
FIGS. 2A-2C show that dysferlin mRNA splicing is altered in patients P1 and P2, leading to inclusion of pathogenic pseudoexon PE50.1.
Figure 2B:
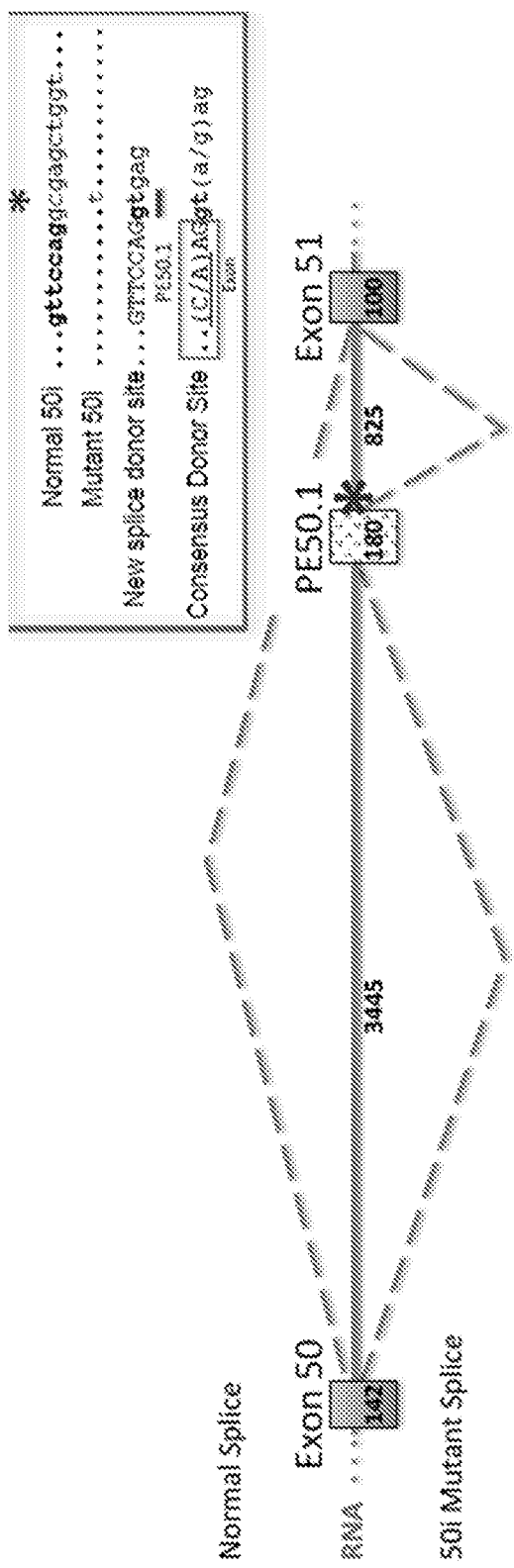
Figure 2C:
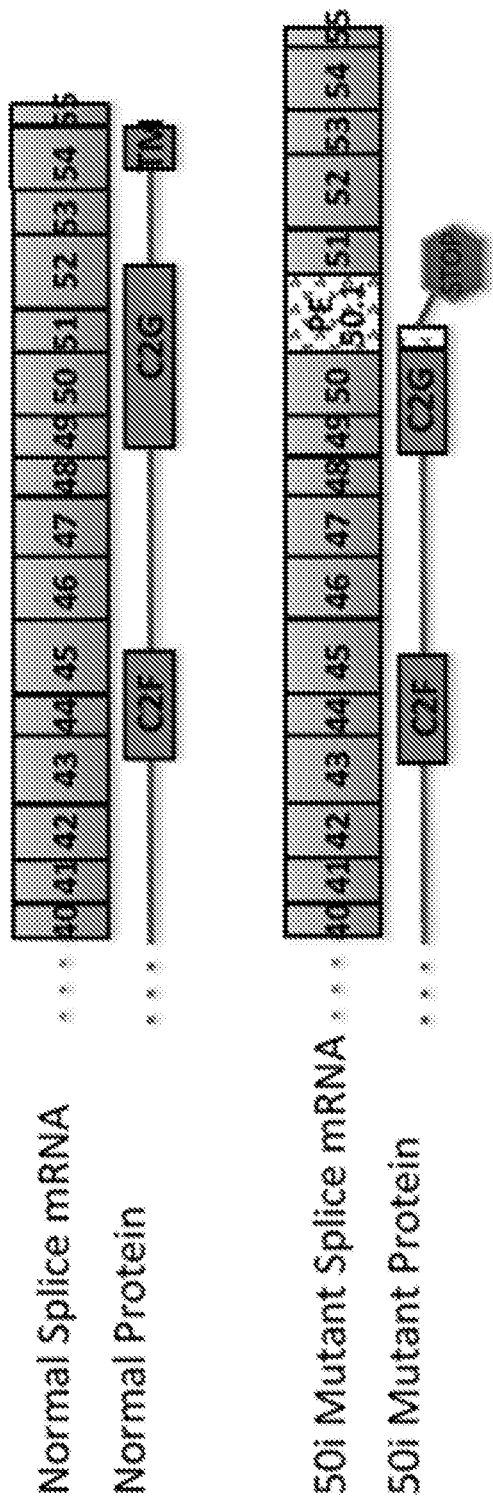

As shown in FIG. 2A, sequence analysis of these RT-PCR products revealed the insertion of 180 base pairs (bp) of additional sequence between DYSF exons 50 and 51. This sequence is present within intron 50i and is aberrantly spliced into the DYSF mRNA as a novel pseudoexon (PE) which is referred to as pseudoexon 50.1 (PE50.1). Sequence analysis of the remainder of the cDNA products confirmed the other known pathogenic variant in these patients (c.5698_5699delAG, exon 51) and revealed no additional novel variants in the coding sequence. Inclusion of PE50.1 in the mRNA transcript leads to insertion of 46 additional amino acids followed by a stop codon by the pseudoexon sequence (FIGS. 2B and 2C). In this aberrantly spliced DYSF transcript that contains PE50.1, translation termination within the DYSF C2G domain, resulting in loss of the C-terminus, which contains the transmembrane domain which is critical for DYSF protein function.

Figure 5:
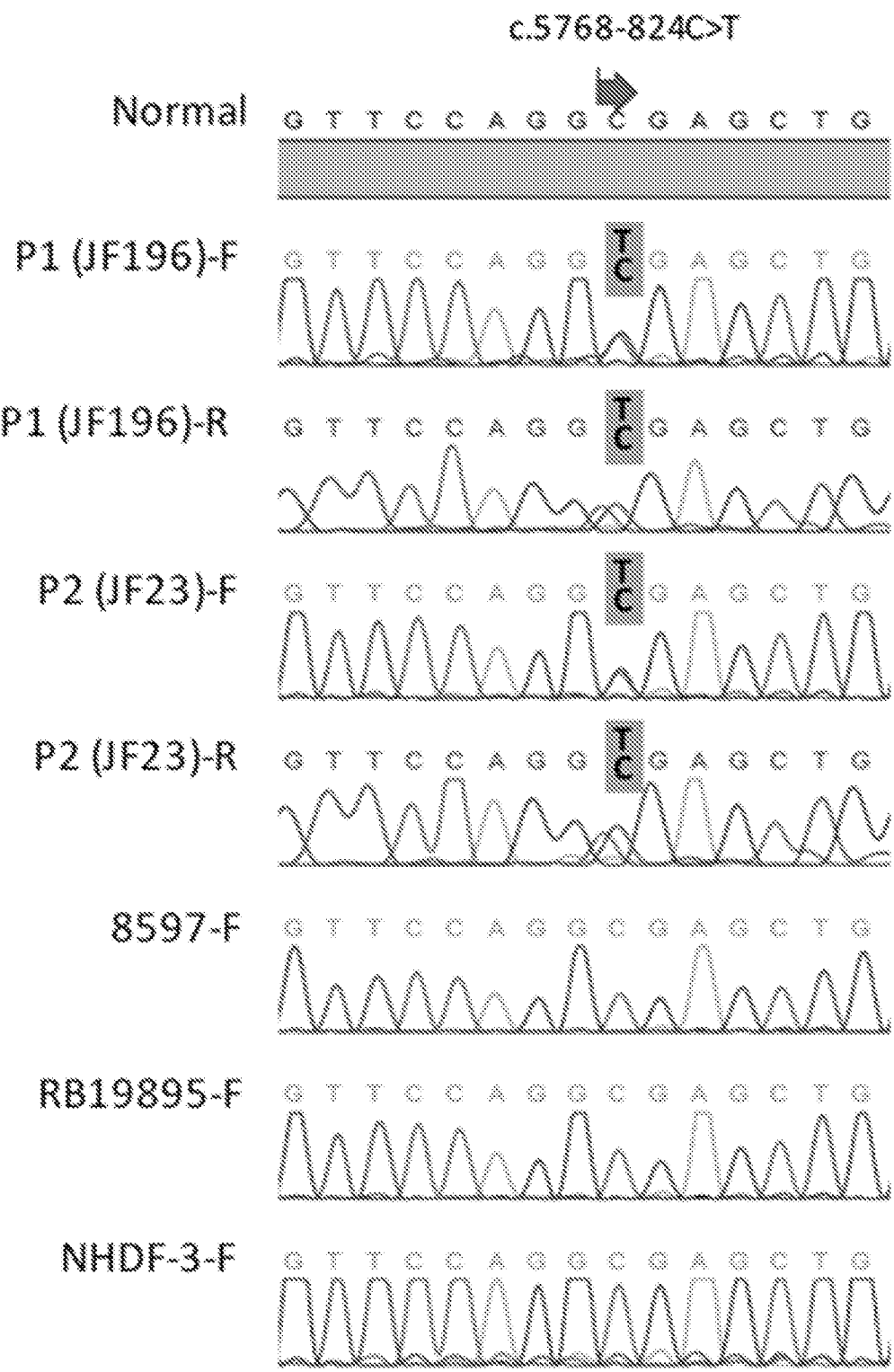
FIG. 5 shows analysis of genomic DNA from patients P1 (JF196) and P2 (JF23), which revealed that both are heterozygous for the c.5768-824C>T mutation deep within DYSF intron 50i. Genomic DNAs from patients' fibroblasts were amplified and sequenced using primer sets that tiled through 50i (Table 4), revealing this mutation in the P1 and P2 cells, but not in fibroblasts from an unrelated patients (8597: patient with other dysferlin mutations, RB19895: amyotrophic lateral sclerosis patient) or normal human dermal fibroblasts (NHDF-3). Samples were sequenced using sense (forward) and antisense (reverse) primers as indicated.
Figure 6:
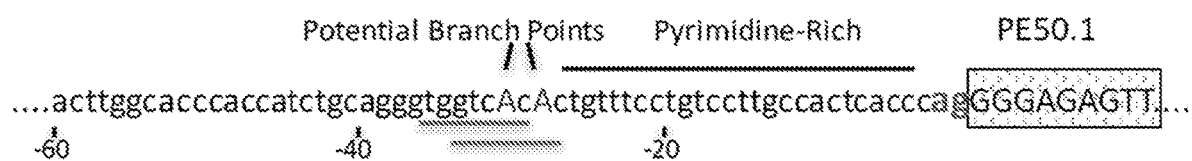
FIG. 6 shows that the intronic sequence upstream of pseudoexon PE50.1 contains additional consensus sites required for mRNA splicing. These include a splice acceptor sequence (ag) at the 5' end of PE50.1, an adjacent pyrimidine-rich region and two potential branch point consensus sequences (underlined) that could be used to promote splicing. These sequences, in the presence of c.5768-824 C>T mutation, likely allow PE50.1 to be spliced between exons 50 and 51.

Further sequence analysis of genomic DNA from these patient cells revealed that PE50.1 inclusion in the mRNA transcripts is caused by a novel point mutation (c.5668-824C>T) deep within intron 50i (FIG. 5). As shown in FIG. 2B, this point mutation creates a consensus splice donor site that promotes the splicing of the 180 bp PE50.1 sequence between exons 50 and 51. Additionally, a consensus "YAG" splice acceptor sequence exists immediately upstream of the PE50.1 sequence, alone with a pyrimidine rich region and potential branch points as predicted by Human Splicing Finder, all of which are critical for splicing (FIG. 6).

Genomic DNA and cDNA from differentiated iFDM cells derived from an unrelated dysferlinopathy patient (TDM57) were analyzed. This unrelated patient also had only one known pathogenic dysferlin variant identified (c.2998T>C). Genomic DNA sequence analysis showed that this patient also carries that c.5668-824C>T point mutation in intron 50i, and RT-PCR analysis of iFDM cell mRNA showed the aberrant inclusion of PE50.1 in the mRNA of this patient. Additionally sequence variants present within intron 50i of patients JF196, JF23, and TDM57 are summarized in Table 1 below. Each of these variants are reported in the dbSNP database and have no known pathogenicity.

TABLE 1

Genomic DNA sequence variants in DYSF intron 50i of dysferlinopathy patients.

| SNP name | Ref. | Var. | JF196 (P1) | JF23 (P2) | TDM57 | NHDF-2 | nt Position | Sequence | Primers | Global MAF | Chromosomal location | SEQ ID NOs |
|---|---|---|---|---|---|---|---|---|---|---|---|---|
| Novel | C | T | C\|T | C\|T | C\|T | C\|C | c.5668-824C>T | TTGTTCCAGG[C/T]GAGCTGGTCT | 50i 10 F + R (SEQ ID NO: 19, 20) | | 2:7167 3373 | 106/107 |
| rs3791829 | A | G | G\|G | G\|G | A\|G | G\|G | c.5667-199A>G | CTGTCTCAGC[A/G]TTGTGTGATG | 50i 1 F + R (SEQ ID NO: 1,2) | A = 0.1 677/840 A = 0.1 425/4148 | 2:7166 9945 | 108/109 |
| rs3791830 | G | A | A\|A | A\|A | G\|A | A\|A | c.5667-1075G>A | TATGCTGGTT[A/G]TTGTGTGATG | 50i 3 F + R (SEQ ID NO: 5, 6) | G = 0.2 298/1151 G = 0.2 242/6527 | 2:7167 0821 | 110/111 |
| rs3791832 | C | A | A\|A | A\|A | C\|A | A\|A | c.5668-2222C>A | GCAGGGGTGG[A/C]GAGGAGGAAG | 50i 6 F + R (SEQ ID NO: 11, 12) | C = 0.2 151/1077 C = 0.2 033/5918 | 2:7167 1975 | 112/113 |
| rs72829766 | C | T | C\|C | C\|C | C\|C | C\|T | c.5668-913C>T | CTGAGGGGTG[C/T]TCCCCGGCCT | 50i 9 F + R (SEQ ID NO: 17, 18) | T = 0.0 505/253 T = 0.0 513/1494 | 2:7167 3284 | 114/115 |
| rs7604764 | G | A | G\|A | G\|A | G\|A | A\|A | c.5668-642G>A | CCTTACAGCA[A/G]CGTGCTGGGA | 50i 10 F + R (SEQ ID NO: 19, 20) | G = 0.4 3.61/2184 G = 0.4 676/13616 | 2:7167 3555 | 116/117 |
| rs13024390 | T | G | T\|G | T\|G | T\|G | G\|G | c.5668-522T>G | AGAGCAGGAC[G/T]CTGGAACCCA | 50i 10 F + R (SEQ ID NO: 19, 20) | T = 0.4 357/2182 T = 0.4 674/13610 | 2:7167 3675 | 118/119 |
| rs882973 | C | T | C\|T | C\|T | C\|T | T\|T | c.5668-366C>T | AGAGGGCCAA[C/T]GCATAGGAAG | 50i 11 F + R (SEQ ID NO: 21,22) | C = 0.2 718/1361 C = 0.2 665/7760 | 2:7167 3831 | 120/121 |
| rs2559081 | C | T | C\|T | C\|T | C\|T | T\|T | c.5668-41C>T | TCTCTCTAAC[C/T]TTGCTTCCTT | 50i 12 F + R (SEQ ID NO: 23, 24) | C = 0.2 720/1362 C = 0.2 660/7743 | 2:7167 4156 | 122/123 |

Genomic variations within DYSF intron 50i in patients are listed. The novel mutation c.5668-824C>T results in PE50.1 inclusion in mature mRNAs. Other variations listed are reported in the dbSNP database and have not been shown to be pathogenic. Global MAF values: top. 1000 Genomes; bottom. TOPMED. The primer sets used to amplify and sequence these regions are shown. The DYSF reference sequence used: GRCh38.p7; mRNA isoform8, NM_003494.3.

Example 2, Additional Dysferlinopathy Patients with the Intron 50i c.5668-824C>T Mutation The genomic DNA was examined from additional dysferlinopathy patients that had only one or neither of their pathogenic variants identified to determine if they carried the 50i c.5668-824C>T intronic variant, including two additional siblings of JF196 and JF23. As summarized in Table 2 below, a total of 22 patients from seventeen families were found to carry this mutation, wherein nine of these patients are homozygous.

TABLE 2

Summary of patients with the new c.5668-824C>T mutation in intron 50i

| Patient ID | Patient Origin | Intron 50i Mutation | Second DYSF Mutation | | Laboratory |
|---|---|---|---|---|---|
| JF23 | UK | c.5668-824C>T | c.5698_5699delAG | 1.5 | Sib- |
| JF196 | UK | c.5668-824C>T | c.5698_5699delAG | 1.5 | lings |
| IGM7 | UK | c.5668-824C>T | c.5698_5699delAG | 5 | |
| IGM8 | UK | c.5668-824C>T | c.5698_5699delAG | 5 | |
| JF404 | USA | c.5668-824C>T | c.2997G>T | 2.4 | Sib- |
| JF1729 | USA | c.5668-824C>T | c.2997G>T | 2 | lings |

TABLE 2-continued

Summary of patients with the new c.5668-824C>T mutation in intron 50i

| Patient ID | Patient Origin | Intron 50i Mutation | Second DYSF Mutation | Laboratory | |
|---|---|---|---|---|---|
| JF4228 | USA | c.5668-824C>T | c.5668-824C>T | 2 | |
| TDM48 | India | c.5668-824C>T | c.5668-824C>T | 3 | |
| TDM57 | India | c.5668-824C>T | c.2998T>C | 1,3 | Siblings |
| TDM58 | India | c.5668-824C>T | c.2998T>C | 3 | |
| TDM63 | India | c.5668-824C>T | c.5668-824C>T | 3 | |
| TDM93 | India | c.5668-824C>T | c.5668-824C>T | 3 | |
| TDM180 | India | c.5668-824C>T | c.5668-824C>T | 3 | |
| TDM182 | India | c.5668-824C>T | c.5668-824C>T | 3 | |
| TDM196 | India | c.5668-824C>T | c.5668-824C>T | 2 | |
| TDM230 | India | c.5668-824C>T | c.1911C>G | 2 | |
| F1-170-1-2 | France | c.5668-824C>T | c.855+1delG | 4 | Siblings |
| F1-170-2-2 | France | c.5668-824C>T | c.855+1delG | 4 | |
| F1-436-1-0 | India | c.5668-824C>T | c.5668-824C>T | 4 | |
| IGM1 | UK | c.5668-824C>T | c.1911C>G | 5 | |
| IGM2 | UK | c.5668-824C>T | c.5668-824C>T | 5 | |
| IGM3 | UK | c.5668-824C>T | c.2434dup | 5 | |
| IGM4 | UK | c.5668-824C>T | c.937+1G>A | 5 | |

The initial patients found to carry the mutation in bold type. Laboratory that identified the patient's mutation: 1-University of Massachusetts Medical School Worcester; 2-Emory University School of Medicine Atlanta; 3-Emory University School of Medicine Atlanta, described in Dastur et al. 2017; 4-Marseille Medical Genetics, Aix Marseille University Marseille; 5-Institue of Genetic Medicine, Newcastle.

Figure 3A:
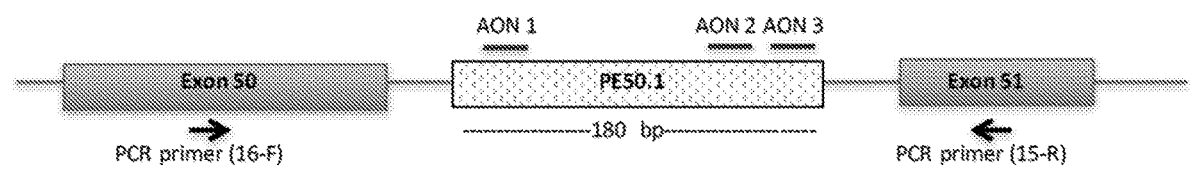
FIGS. 3A-3B show antisense oligonucleotide-mediated skipping of PE50.1 in patient iFDM cells.
Figure 3B:
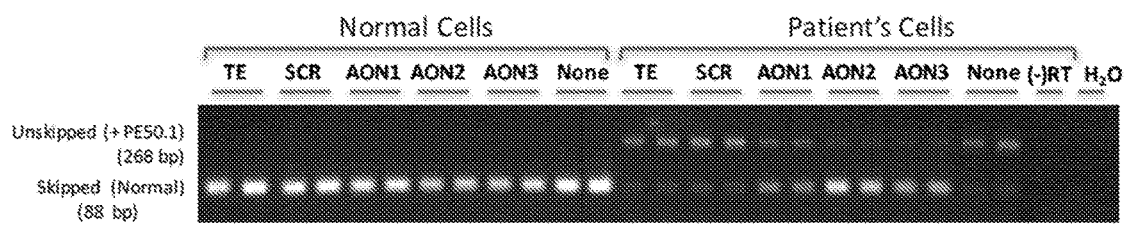

Example 3, Antisense Oligonucleotides Targeting PE50.1 Restore Production of Normal DYSF mRNA Given that aberrant splicing caused by the c.5668-824C>T intron 50i mutation leads to inclusion of the disruptive PE50.1 sequence, blocking this aberrant splicing should restore normal DYSF RNA and protein. Three antisense oligonucleotides (AONs) were designed targeting different possible exonic splice enhancer (ESE) regions within PE50.1 that could promote PE50.1 splicing into the mature mRNA. Therefore, targeting these ESEs with AONs would prevent PE50.1 inclusion. RT-PCR analysis of patient's iFDM myotubes treated for two days with AONs reveals that AONs indeed inhibit expression of the mutant PE50.1 DYSF mRNA spliced form and restore higher levels of the normal mRNA splice form that lacks PE50.1 (FIG. 3).

Figure 4A:
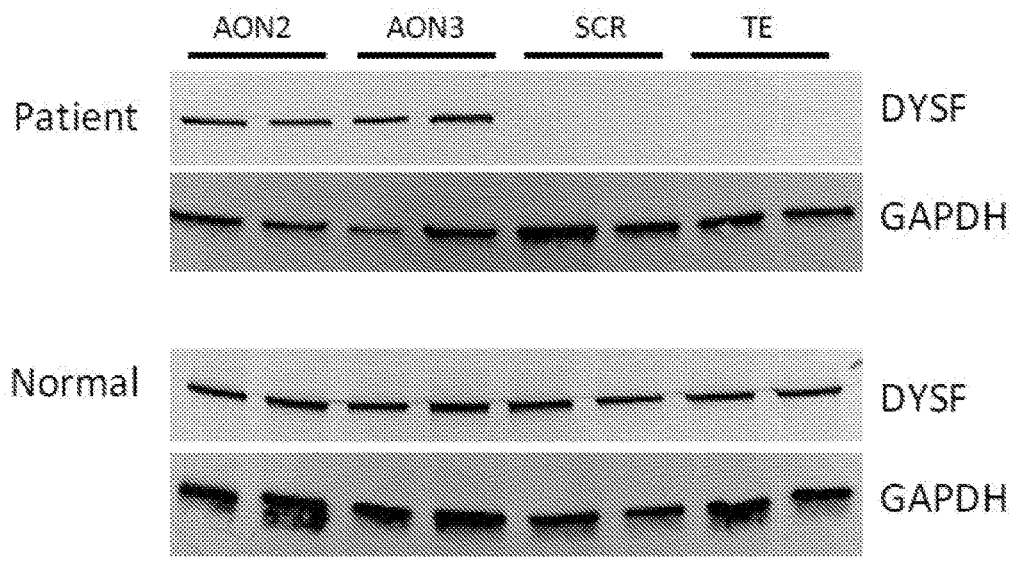
FIGS. 4A-4B show that treatment of patient iFDM cells with AON2 and AON3 directed to PE50.1 induces dysferlin protein expression. iFDM cells (duplicate cultures) were allowed to differentiate in DM for 6 days then treated with AONs in DM (or TE buffer as controls) for 3 days, and cells were collected for protein analysis 7 days after AON addition.
Figure 4B:
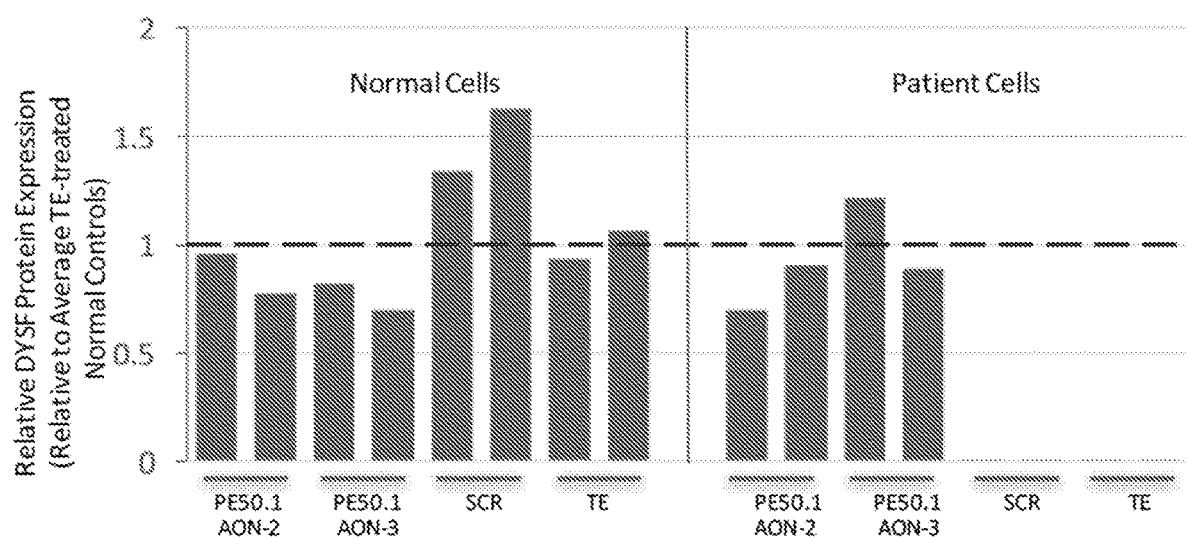

The presence and absence of PE50.1 in the mRNA transcripts was confirmed by sequencing the larger and smaller RT-PCR products, respectively. AON treatment for three days (followed by four days without AONs) also restored DYSF protein expression to levels similar to that in normal myotubes (FIG. 4), likely as a result of the higher amounts of normally-spliced transcripts induced by PE50.1-skipping. The premature translational stop codon within PE50.1 likely leads to nonsense-mediated mRNA decay, whereby mRNA carrying a premature stop codon is transcribed and spliced but degraded during the translation process, leading to reduced mRNA levels (typically detectable using sensitive RT-PCR methods) along with aborted protein synthesis. The overall reduced levels of RT-PCR products observed in untreated or control-treated patient cells compared with normal cells (FIG. 3) is consistent with this. It is unlikely that the mutation leads to significant synthesis of a truncated protein be expression of a shorter DYSF protein is not detected on Western blots using an antibody specific to the DYSF N-terminal region (data not shown).

Methods for Examples 1-3

Patients. Samples used in this study (blood or skin biopsy samples) were from patients clinically diagnosed as either distal dominant Miyoshi myopathy (MM) or proximal dominant limb-girdle muscular dystrophy (LGMD) 2B dysferlinopathies. These patients exhibited progressive limb muscle weakness beginning in adolescence or early adulthood, elevated blood creatine kinase levels indicating muscle damage, and demonstrated reduced or absent dysferlin protein expression in muscle biopsies and/or blood monocyte cells when screened. Patient materials were collected in accordance with ethical guidelines and protocols approved by the University of Massachusetts Medical School Institutional Review Board, and similar review boards at Emory University School of Medicine, Aix-Marseille University, or Institute of Genetic Medicine, Newcastle. For all of the patients described, only one or neither of the pathogenic variants had been defined by exon sequencing. The dysferlinopathy patients initially screened, JF196 and JF23 (designated P1 and P2, respectively), are siblings participating in an ongoing international "Clinical Outcome Study for Dysferlinopathy", a collaboration with the Jain Foundation and Newcastle upon Tyne Hospitals. Patient skin fibroblasts were obtained from the Newcastle-upon-Tyne Hospital BioBank. These patients are heterozygous for one pathogenic dysferlin variant identified by exon sequencing (c.5698_5699delAG), but the other pathogenic allele had not been identified. Similarly, dysferlinopathy patient TDM57 had only one pathogenic allele defined by exon sequencing (c.2998T>C). TDM57 skin biopsy tissue was obtained via the Jain Foundation as part of a diagnostic program at the Centre for Advanced Molecular Diagnostics in Neuromuscular Disorders, Mumbai, Maharashtra, India. TDM57 and other TDM patients reported here (except TDM196 and TDM230) were described previously. All TDM patient genomic DNA was sequenced at Emory University School of Medicine as described. Additional patient genomic DNA sequencing was performed at Aix-Marseille University or Newcastle-upon-Tyne Hospitals. Fibroblasts from unrelated individuals served as DNA sequence analysis controls (8597: dysferlinopathy patient with different dysferlin mutations; NHDF-3: normal; RB19895: amyotrophic lateral sclerosis patient).

Cell culture. Skin biopsy samples were placed in culture dishes to establish fibroblast cultures. We obtained normal adult human dermal fibroblasts (termed NHDF-2 and NHDF-3 cells) from the American Type Culture Collection (ATCC, Manassas, VA, USA). Fibroblasts were transduced with lentivirus vectors carrying tamoxifen-inducible MyoD to generate inducible fibroblast-derived myogenic cells (iF-DMs). These cells proliferate as fibroblasts and can be induced to differentiate into myotubes by treatment with 4-hydroxytamoxifen (TMX). TMX induces MyoD expression and myotube formation when cells are cultured in low serum differentiation medium (DM) ((DMEM Glutamax with pyruvate: Medium 199 (Gibco, Grand Island, NY, USA) (3:1), 2% horse serum (HyClone, Logan UT, USA), 20 mM HEPES, and 20 μg/mL insulin, 11 μg/mL transferrin, 1.3 μg/mL selenium (2×ITS, Gibco)).

Nucleic acid purification. Genomic DNA was purified from cells using Gentra Puregene (Qiagen, Valenica, CA, USA) reagents following manufacturers' protocols. RNA was purified from patient and normal iFDM cells using TRIzol reagent (Life Technologies, Grand Island, NY, USA), digested with DNAse (TURBO DNA-Free, Ambion, Austin, TX, USA) to remove contaminating DNA, then RNA was reverse transcribed (High Capacity cDNA Reverse Transcription Kit, Applied Biosystems Foster City, CA, USA) using manufacturers' protocols to generate cDNA for PCR analyses. For all analyses, DYSF mRNA variant 8 (NM_003494.3), the predominant skeletal muscle isoform was used as the reference sequence.

PCR amplification. PCR was used to amplify and sequence the complete dysferlin cDNA derived from myogenic cell (iFDM cell) RNA. For this, 17 primer sets generating 450-500 bp amplicons that tiled across the DYSF cDNA were used as described to sequence and screen the cDNA for mutations. Additionally, 12 primer sets (Table 4) that tiled across DYSF intron 50i were used to sequence and screen the patient genomic DNA for variants. Additional primers (Table 4) that can be used to sequence patient DNA for the mutated sequence are also listed. M13 sequence tails were added to primers to facilitate sequencing (Table 4).

Antisense oligonucleotide treatment of cell cultures. Antisense oligonucleotides (AONs) were designed that target potential exonic splicing enhancer (ESE) sequences within PE50.1 using Human Splicing Finder v.3.0 and Rescue-ESE online tools. Blocking these ESEs within AONs could inhibit the splicing of PE50.1 into mature processed mRNAs, thereby leading to the synthesis of normally-spliced DYSF transcripts. Three AONs targeting PE50.1 (Table 5) were used along with a non-specific scrambled AON control (SCR). These AONs were synthesized as 2'-O-methyl RNA with full-length phosphorothioate backbones (Integrated DNA Technologies, Coralville, IA, USA). iFDM cells derived from patients JF196 (P1), JF23 (P2), and normal NHDF-2 fibroblasts were allowed to differentiate for the indicated lengths of time to form myotubes. Cells were transfected with AON (600 nM) (or TE buffer as control) using Oligofectamine (Life Technologies) and the manufacturers' protocol. After the indicated times, RNA was extracted and evaluated by RT-PCR using primers (SEQ ID NOs: 30 & 31) to amplify either the normal DYSF sequence (88 bp) or the mutant version containing pseudoexon50.1 (PE50.1) (268 bp). Proteins were extracted from similar cultures and evaluated on Western blots using antibodies against the dysferlin C-terminal region (NCL-Hamlet, Leica, Buffalo Grove, IL, USA, 1/1000) and GADPH (G9545, Sigma, St. Louis, MO, USA, 1/1000) as described. Protein expression levels were calculated from Western blot images using a Li—COR Odyssey infrared imager and Image Studio Software (Li—COR).

TABLE 3

Primers (forward (F) and reverse (R)) used to generate overlapping amplicons that span entire dysferlin cDNA.

| Primer Name | Sequence | SEQ ID NO: |
|---|---|---|
| 1F | AGGTGCAAAATGCCGTGT | 1 |
| 1R | TTCACCCCTGCAAACACC | 2 |
| 2F | CACACCCGACACCGACAT | 3 |
| 2R | CTCCGCCTCATCTCCAGTG | 4 |
| 3F | CGACTCTGCCTGACCTGGA | 5 |
| 3R | AATGGTGCCCACGTCCAT | 6 |
| 4F | TCGTTCTCTCAGGACAGATGC | 7 |
| 4R | CTGAGGGTTGGCCGTCTT | 8 |
| 5F | GACCCCTTTGTGGAGGTCA | 9 |
| 5R | GCTCCACCAGCTTGGTCTC | 10 |
| 6F | GGGGGAAGGTGTGGCTTAT | 11 |
| 6R | CAGCGAGTCCACGTCCTC | 12 |
| 7F | CCAGCTGCTTGGGATTGC | 13 |
| 7R | TCCCACAATTCTTGCCACA | 14 |
| 8F | GCCCACCAAGTCCTCTTCTC | 15 |
| 8R | AAGCCGGGTCTGGTTCTC | 16 |
| 9F | TCACCTGAGCTTCGTGGAA | 17 |
| 9R | TTCTCCAGTGGCTCCATGC | 18 |
| 10F | CCACCTCGAGTACCGCAAG | 19 |
| 10R | CGTACAGCTCCACCACAATG | 20 |
| 11F | AACACCCTTAACCCCACCTG | 21 |
| 11R | CGGAGGTTCCTGATGACACA | 22 |
| 12F | CCCCAGCCTCGTGGTAGA | 23 |
| 12R | ACCTTCAGGGTGTCAAAATCC | 24 |
| 13F | TGCCTCCATAGGGGAGAGG | 25 |
| 13R | TGCAGGTCAGCTCGAACA | 26 |
| 14F | TGGAGCCCGTATTTGGAA | 27 |
| 14R | TGCAGGGGCTGTAGAGG | 28 |
| 15F | CGTCTGGCTCTGCATGTG | 29 |
| 15R | CCACTCGTGCTGGGATTTT | 30 |
| 16F | CTGCCAGCTGAGCAAGTCTG | 31 |
| 16R | GCCGCCACAGGATGAACT | 32 |
| 17F | CCGACACCTCCTTCCTGTG | 33 |
| 17R | TTGTGGTTCCAACTGTTTTATACTGA | 34 |

TABLE 4

Primers (forward (F) and reverse (R)) used to generate overlapping amplicons that span dysferlin intron 50i, and an additional primer set (PE50.1-F, PE50.1-R) for genotyping.

| Primer Name | Sequence | SEQ ID NO: |
| --- | --- | --- |
| 50i.1F | TGGGAGGTGAAGGCAACTT | 35 |
| 50i.1R | TGGAAAAGGGGTGGATGC | 36 |
| 50i.2F | TCATGGCACTACCGTGGTC | 37 |
| 50i.2R | GGAGGGTGATGGCTGTGG | 38 |
| 50i.3F | GCCTATGGTCACCGTCCA | 39 |
| 50i.3R | AATCGGGCCAGCAGAATC | 40 |
| 50i.4F | GTCCCACCCGGCATTAAA | 41 |
| 50i.4R | TTGGGGCAGATGCAACCT | 42 |
| 50i.5F | GAAAGCATGGGCCGTTTG | 43 |
| 50i.5R | AATGGAGCCACCCCAAAT | 44 |
| 50i.6F | AGAGAGGGTTACCCGGCAGT | 45 |
| 50i.6R | GTTTCTGTCTCCGCCTTCG | 46 |
| 50i.7F | GGGAGAAGGTGGCTGGAA | 47 |
| 50i.7R | CTGACGTGCAGGGTGTGC | 48 |
| 50i.8F | GCGGCTTTGAACCACCAC | 49 |
| 50i.8R | AGCTCCCGAACCGAAGAC | 50 |
| 50i.9F | CCAACCCAGGCAGCAGTC | 51 |
| 50i.9R | CAGCTCGCCTGGAACAAG | 52 |
| 50i.10F | CAGTCCCACACCGCTCAG | 53 |
| 50i.10R | TATGCGTTGGCCCTCTACTG | 54 |
| 50i.11F | CAGCTGCCAGGGTTTGAG | 55 |
| 50i.11R | GGATGCAAGGAAGCAAGGT | 56 |
| 50i.12F | CCCTTGGGGACATCCTACTC | 57 |
| 50i.12R | ACTTGCGTCCCTCGCTTAC | 58 |
| PE50.1-F | CCCGGCACTCAGGACTTG | 59 |
| PE50.1-R | TGCTGGGAAGTTCCGTCTC | 60 |
| M13-F | GTAAAACGACGGCCAGT | 61 |
| M13-R | CAGGAAACAGCTATGAC | 62 |

TABLE 5

AONs targeting human exonic splicing enhancer sequences (ESE) in DYSF PE50.1. AONs for in vitro studies are 2'-O-methyl RNA with full-length phosphorothioate backbones.

| Primer Name | AON Sequence | SEQ ID NO: | Target Sequence | SEQ ID NO: |
| --- | --- | --- | --- | --- |
| AON1 | AGUCUUGUUCUCUGUUUUCUCA | 63 | TGAGAAAACAGAGAACAAGACT | 64 |
| AON2 | ACUGAGGCUUCAUGGAGCAAC | 65 | GTTGCTCCATGAAGCCTCAGT | 66 |
| AON3 | GGUCAUCUUGGGCUUCCUCCCAC | 67 | GTGGGAGGAAGCCCAAGATGACC | 68 |

TABLE 6

AONs to effect pseudoexon PE50.1 expression and ability to enhance expression of normal dysferlin mRNA and protein.

| Primer Name | AON Sequence | SEQ ID NO: | Target Sequence | SEQ ID NO: |
| --- | --- | --- | --- | --- |
| AON4 | CGGAGGCCGGGGAGCACCCCUCAG | 69 | CTGAGGGGTGCTCCCCGGCCTCCG | 70 |
| AON5 | GAGCAAGGGCCUGGACCCAACUCU | 71 | AGAGTTGGGTCCAGGCCCTTGCTC | 72 |
| AON6 | CCAAGUCCUGAGUGCCGGGUCAGA | 73 | TCTGACCCGGCACTCAGGACTTGG | 74 |
| AON7 | GACCACCCUGCAGAUGGUGGGUGC | 75 | GCACCCACCATCTGCAGGGTGGTC | 76 |
| AON8 | UGGCAAGGACAGGAAACAGUGUGA | 77 | TCACACTGTTTCCTGTCCTTGCCA | 78 |
| AON9 | ACUAUAACUCUCCCCUGGGUGAGU | 79 | ACTCACCCAGGGGAGAGTTATAGT | 80 |
| AON10 | GUCACUAGGGCUUUCCAGCGCAGU | 81 | ACTGCGCTGGAAAGCCCTAGTGA | 82 |

TABLE 6-continued

AONs to effect pseudoexon PE50.1 expression and ability to enhance expression of normal dysferlin mRNA and protein.

| Primer Name | AON Sequence | SEQ ID NO: | Target Sequence | SEQ ID NO: |
|---|---|---|---|---|
| AON11 | CCACACUCAACCCACAGCACUGUC | 83 | GACAGTGCTGTGGGTTGAGTGTGG | 84 |
| AON12 | ACCCCUCAGUCCAGCCACACUCAA | 85 | TTGAGTGTGGCTGGACTGAGGGGT | 86 |
| AON13 | UGAGCGGUGUGGGACUGCACAUGC | 87 | GCATGTGCAGTCCCACACCGCTCA | 88 |
| AON14 | GGGCUUCCUCCCACUGAGGCUUCA | 89 | TGAAGCCTCAGTGGGAGGAAGCCC | 90 |
| AON15 | AGGUCAUCUUGGGCUUCCUCCCAC | 91 | GTGGGAGGAAGCCCAAGATGACCT | 92 |
| AON16 | UCAGACCAGCUCGCCUGGAACAAG | 93 | CTTGTTCCAGGCGAGCTGGTCTGA | 94 |
| AON17 | UUCUCUCCCCACCCCACCUCCCUC | 95 | GAGGGAGGTGGGGTGGGGAGAGAA | 96 |
| AON18 | GCUGAAAGGAGAGGAGGGGCCCUU | 97 | AAGGGCCCCTCCTCTCCTTTCAGC | 98 |
| AON19 | AGUGCUGGGAAGUUCCGUCUCCUG | 99 | CAGGAGACGGAACTTCCCAGCACT | 100 |
| AON20 | GGGCAAAGCCAAAGCCUGAAGUGC | 101 | GCACTTCAGGCTTTGGCTTTGCCC | 102 |

ADDITIONAL SEQUENCES

>Pseudoexon 50i.1:
SEQ ID NO: 103
GGGAGAGTTATAGTGAGAAAACAGAGAACAAGACTGCGCTGGAAAGC
CCTAGTGACAGTGCTGTGGGTTGAGTGTGGCTGGACTGAGGGGTGCT
CCCCGGCCTCCGCATGTGCAGTCCCACACCGCTCAGTTGCTCCATGA
AGCCTCAGTGGGAGGAAGCCCAAGATGACCTTGTTCCAG >Intron 50 in the context of a c.5668-824 (C>T):
SEQ ID NO: 104
CACCATCTGCAGGGTGGTCACACTGTTTCCTGTCCTTGCCACTCACC
CAGGGGAGAGTTATAGTGAGAAAACAGAGAACAAGACTGCGCTGGAA
AGCCCTAGTGACAGTGCTGTGGGTTGAGTGTGGCTGGACTGAGGGGT
GCTCCCCGGCCTCCGCATGTGCAGTCCCACACCGCTCAGTTGCTCCA
TGAAGCCTCAGTGGGAGGAAGCCCAAGATGACCTTGTTCCAGG(c/t)
AGCTGGTCTGAGGGAGGTGGGGTGGGAGAGAAGGGCCCCTCCTCTC >Intron 50:
SEQ ID NO: 105
CACCATCTGCAGGGTGGTCACACTGTTTCCTGTCCTTGCCACTCACC
CAGGGGAGAGTTATAGTGAGAAAACAGAGAACAAGACTGCGCTGGAA
AGCCCTAGTGACAGTGCTGTGGGTTGAGTGTGGCTGGACTGAGGGGT
GCTCCCCGGCCTCCGCATGTGCAGTCCCACACCGCTCAGTTGCTCCA
TGAAGCCTCAGTGGGAGGAAGCCCAAGATGACCTTGTTCCAGGAGCT
GGTCTGAGGGAGGTGGGGTGGGAGAGAAGGGCCCCTCCTCTC While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. An oligonucleotide comprising 10 to 25 nucleotides in length comprising a region of complementarity that is complementary with at least 8 contiguous nucleotides of a sequence within a region between exons 50 and 51 encoded by a human DYSF gene, wherein the oligonucleotide comprises at least one modified nucleotide or at least one modified internucleotide linkage, wherein the human DYSF gene comprises a c.5668-824 (C>T) mutation.

2. The oligonucleotide of claim 1, wherein the oligonucleotide consists of 10-25 nucleotides in length.

3. The oligonucleotide of claim 1, wherein the oligonucleotide comprises 20-25 nucleotides in length.

4. The oligonucleotide of claim 1, wherein the region of complementarity is complementary with 8-25 contiguous nucleotides of a sequence within a region between exons 50 and 51 encoded by a human DYSF gene.

5. The oligonucleotide of claim 1, wherein the region of complementarity is complementary with 15-25 contiguous nucleotides of a sequence within a region between exons 50 and 51 encoded by a human DYSF gene 10-25 nucleotides in length.

6. The oligonucleotide of claim 1, wherein the region of complementarity is complementary with at least 8 contiguous nucleotides of a sequence as set forth in SEQ ID NO: 104.

7. The oligonucleotide of claim 1, wherein the region of complementarity is complementary with 8-25 contiguous nucleotides of a sequence as set forth in SEQ ID NO: 104.

8. The oligonucleotide of claim 1, wherein the region of complementarity is complementary with 15-25 contiguous nucleotides of a sequence as set forth in SEQ ID NO: 104.

9. The oligonucleotide of claim 1, wherein the oligonucleotide comprises at least one modified nucleotide.

10. The oligonucleotide of claim 9, wherein the at least one modified nucleotide is a 2'-modified nucleotide.

11. The oligonucleotide of claim 10, wherein the 2'-modified nucleotide is a 2'-deoxy, 2'-fluoro, 2'-O-methyl, 2'-O-methoxyethyl, 2'-amino, or 2'-aminoalkoxy modified nucleotide.

12. The oligonucleotide of claim 10, wherein the 2'-modified nucleotide comprises a 2'-O-4'-C methylene bridge.

13. A pharmaceutical composition comprising the oligonucleotide of claim 1 and a pharmaceutically-acceptable carrier.

14. An expression construct encoding the oligonucleotide of claim 1.

15. A recombinant AAV comprising the expression construct of claim 14.

16. A method of modulating splicing in a cell that contains a DYSF gene comprising a c.5668-824 (C>T) mutation, the method comprising:
    delivering to the cell an oligonucleotide comprising 10 to 25 nucleotides in length comprising a region of complementarity that is complementary with at least 8 contiguous nucleotides of a sequence within a region between exons 50 and 51 encoded by a human DYSF gene, wherein the oligonucleotide comprises at least one modified nucleotide or at least one modified internucleotide linkage.

* * * * *